US005656427A

United States Patent [19]
Hammond et al.

[11] Patent Number: 5,656,427
[45] Date of Patent: Aug. 12, 1997

[54] **NUCLEIC ACID HYBRIDIZATION ASSAY PROBES, HELPER PROBES AND AMPLIFICATION OLIGONUCLEOTIDES TARGETED TO *MYCOPLASMA PNEUMONIAE* NUCLEIC ACID**

[75] Inventors: Philip W. Hammond, Tehachapi; Anthony A. Endozo, Temecula, both of Calif.

[73] Assignee: Gen-Probe Incorporated, San Diego, Calif.

[21] Appl. No.: 297,299

[22] Filed: Aug. 29, 1994

[51] Int. Cl.$^6$ .......................... C07H 21/02; C07H 21/04; C12Q 1/68; C12P 19/34
[52] U.S. Cl. ......................... 435/6; 536/23.1; 536/24.3; 536/24.32; 435/91.2
[58] Field of Search .................... 435/6, 91.2; 536/24.32, 536/24.3, 23.1

[56] References Cited

U.S. PATENT DOCUMENTS

| | | | |
|---|---|---|---|
| 4,851,330 | 7/1989 | Kohne | 435/6 |
| 5,030,557 | 7/1991 | Hogan et al. | 435/6 |
| 5,225,324 | 7/1993 | McFadden et al. | 435/6 |
| 5,288,611 | 2/1994 | Kohne | 435/6 |
| 5,409,818 | 4/1995 | Davey et al. | 435/91.21 |
| 5,552,279 | 9/1996 | Weisburg et al. | 435/6 |

FOREIGN PATENT DOCUMENTS

| | | |
|---|---|---|
| 0250662 | 1/1988 | European Pat. Off. |
| 0305145 | 3/1989 | European Pat. Off. |
| 0318245 | 5/1989 | European Pat. Off. |
| 0398677 | 11/1990 | European Pat. Off. |
| 0524864 | 1/1993 | European Pat. Off. |
| 0528306 | 2/1993 | European Pat. Off. |
| 0576742 | 1/1994 | European Pat. Off. |
| 0576743 | 1/1994 | European Pat. Off. |
| 8803957 | 6/1988 | WIPO. |
| 8906704 | 7/1989 | WIPO. |
| 9002798 | 3/1990 | WIPO. |
| 9100926 | 1/1991 | WIPO. |
| 9215672 | 9/1992 | WIPO. |
| 9222641 | 12/1992 | WIPO. |
| 9304201 | 3/1993 | WIPO. |
| 9305147 | 3/1993 | WIPO. |
| 9322461 | 11/1993 | WIPO. |
| 9322457 | 11/1993 | WIPO. |
| 9403634 | 2/1994 | WIPO. |

OTHER PUBLICATIONS

Advanced Gene Computing Technologies Product Description.

Barone et al., "In situ activities of bis–dialkylaminophosphines—a new method for synthesizing deoxyoligonucleotides on polymer supports," *Nucleic Acids Research* 12:4051–4061 (1984).

Bernet et al., "Detection of *Mycoplasma pneumoniae* by Using the Polymerase Chain Reaction," *J. Clin. Microbiol.* 27:2492–2496 (1989).

Böddinghaus et al., "Phylogenetic analysis and identification of different serovars of *Mycobacterium intracellulare* at the molecular level," *FEMS Microbiol. Letters* 70:197–204 (1990).

Buck et al., "Rapid, Sensitive Detection of *Mycoplasma pneumoniae* in Simulated Clinical Specimens by DNA Amplification," *J. Clin. Microbiol.* 30:3280–3283 (1992).

Cox et al., "The 16S ribosomal RNA of *Mycobacterium leprae* contains a unique sequence which can be used for identification by the polymerase chain reaction," *J. Med. Microbiol.*, 35:284–290 (1991).

Cregan et al., "Use of DNA Probes to Detect *Mycobacterium intracellulare* and X Mycobacteria among Clinical Isolates of *Mycobacterium avium* Complex," *J. Infect. Dis.* 166:191–194 (1992).

Deng et al., "Detection by PCR and Differentiation by Restriction Fragment Length Polymorphism of *Acholeplasma, Spiroplasma, Mycoplasma,* and *Ureaplasma*, Based upon 16s rRNA Genes," *PCR Methods and Applications* 1:202–204 (1992).

Frothingham and Wilson, "Sequence–Based Differentiation of Strains in the *Mycobacterium avium* Complex," *J. Bacter.* 175:2818–2825 (1993).

Göbel et al., "Oligonucleotide Probes Complementary to Variable Regions of Ribosomal RNA Discriminate between *Mycoplasma* Species," *Journal of General Microbiology* 133:1969–1974 (1987).

Göbel and Stanbridge, "Cloned Mycoplasm Ribosomal RNA Genes for the Detection of Mycoplasma Contamination in Tissue Cultures," *Science* 226:1211–1213 (1984).

Hyman et al., "DNA Probes for Detection and Identification of *Mycoplasma pneumonoiae* and *Mycoplasma genitalium*," *J. Clin. Microbiol.* 25:726–728 (1987).

Jensen et al., "Detection of *Mycoplasma pneumoniae* in simulated clinical samples by Polymerase Chain Reaction," *APMIS* 97:1046–1048 (1989).

Kai et al., "Rapid detection of *Mycoplasma pneumoniae* in clinical samples by the polymerase chain reaction," *J. Med. Microbiol.* 38:166–170 (1993).

Lebrun et al., "Evaluation of Nonradioactive DNA Probes for Identification of Mycobacteria,"*J. Clin. Microbiol.* 30:2476–2478 (1992).

Lim et al., "Genotypic Identification of Pathogenic *Mycobacterium* Species by Using a Nonradioactive Oligonucleotide Probe," *J. Clin. Microbiol.* 29:1276–1278 (1991).

Mitsuhashi et al., "Oligonucleotide Probe Design—A New Approach," *Nature* 367:759–761 (1994).

(List continued on next page.)

*Primary Examiner*—Stephanie W. Zitomer
*Assistant Examiner*—Ethan Whisenant
*Attorney, Agent, or Firm*—Lyon & Lyon LLP

[57] ABSTRACT

The present invention describes oligonucleotides targeted to *Mycoplasma pneumoniae* nucleic acid sequences which are particularly useful to aid in detecting *Mycoplasma pneumoniae*. The oligonucleotides can aid in detecting *Mycoplasma pneumoniae* in different ways such as by acting as hybridization assay probes, helper probes, and/or amplification primers.

24 Claims, No Drawings

OTHER PUBLICATIONS

Potera, "Hitachi Chemical Offers Probe Design Software and Service," *Genetic Engineering News* vol. 13 (1993) (reprint—Mary Ann Liebert, Inc. publishers, NY).

Roberts et al., "DNA Probes for the Detection of Mycoplasmas in Genital Specimens," *Israel Journal of Medical Sciences* 23:618–620 (1987).

Rogall et al., "Towards a Phylogeny and Definition of Species at the Molecular Level within the Genus *Mycobacterium*," *International Journal of Systematic Bacteriology* 40:323–330 (1990).

Rogers et al., "Construction of the mycoplasma evolutionary tree from 5S rRNA sequence data," *Proc. Natl. Acad. Sci. USA* 82:1160–1164 (1985).

Tilton, "DNA Probe versus Culture for Detection of *Mycoplasma pneumoniae* in Cllinical Specimens," *Diagn. Microbiol. Infec. Dis.* 10:109–112 (1988).

van Kuppeveld et al., "Genus– and Species–Specific Identification of Mycoplasmas by 16S rRNA Amplification," *Applied and Envir. Microbiol.* 58:2606–2615 (1992).

van Kuppeveld et al., "Genus– and Species–Specific Identification of Mycoplasmas by 16S rRNA Amplification—Author's Correction," *Applied and Envir. Microbiol.* 59:655 (1993).

Weisburg et al., "A Phylogenetic Analysis of the Mycoplasmas: Basis for Their Classification," *Journal of Bacteriology* 171:6455–6467 (1989).

Yogev et al., "Distinction of Species and Strains of Mycoplasmas (Mollicutes) by Genomic DNA Fingerprints with an rRNA Gene Probe," *J. Clin. Microbiol.* 26:1198–1201 (1988).

Database EMBL European Bioinformatics Institute, Cambridge, UK, Accesion Number EO4364, XP002004222 & JP A–05–051–399 (Oriental Yeast Co.), Mar. 2, 1993.

Ludwig et al., "Complete 23S Ribosomal RNA Sequences of Gram–positive Bacteria with a Low DNA G+C Content," *System Appl. Microbiol.* 15:487–501 (1992).

Peterson et al., "A random sequencing approach for placing markers on the physical map of *Mycoplasma genitalium*," *Nucleic Acids Research* 21:6027–6031 (1991).

Database EMBL European Bioinformatics Institute, Cambridge UK, Accession Number X77334, Mar. 10, 1994, XP002004233 Sequence and Borre et al.

Kawasaki pp. 21–27 in "PCR protocols," Ed. Innis et al. Academic press (1990).

Gingeras et al. pp. 245–252 in "PCR protocols," Ed. Innis et al. Academic press (1990).

Weisburg et al. J. of Bacteriology 171 (12):PP. 6455–6467.

Ludwig et al. Syst. Appl. Microbiol. 15 :pp. 487–501 (1992).

"Basic Methods in Molecular Biology," Ed. Davis et al. Elsevier Sci. Pub. pp. 68–78 (1986).

NUCLEIC ACID HYBRIDIZATION ASSAY PROBES, HELPER PROBES AND AMPLIFICATION OLIGONUCLEOTIDES TARGETED TO MYCOPLASMA PNEUMONIAE NUCLEIC ACID

FIELD OF THE INVENTION

The invention described and claimed herein relates to the design and use of oligonucleotides targeted to *Mycoplasma pneumoniae* nucleic acid. Different types of oligonucleotides are described including hybridization assay probes, helper probes, and amplification oligonucleotides. The oligonucleotides are particularly useful for detecting the species *Mycoplasma pneumoniae* in test samples, such as from throat swabs, tissue samples, body fluids, experimental solutions and cultures.

BACKGROUND OF THE INVENTION

Single strands of deoxyribo- ("DNA") or ribo-("RNA") nucleic acid, formed from nucleotides including the bases adenine (A), cytosine (C), thymidine (T), guanine (G), uracil (U), or inosine (I), may hybridize to form a double-stranded structure held together by hydrogen bonds between pairs of complementary bases. Generally, A is hydrogen bonded to T or U, while G or I are hydrogen bonded to C. Along the chain, classical base pairs AT or AU, TA or UA, GC, or CG are present. Additionally, some mismatched base pairs (e.g., AG, GU) may be present.

Bringing together two single strands of nucleic acid containing sufficient contiguous complementary bases, under conditions which promote their hybridization, results in double-stranded nucleic acid. Under appropriate conditions, DNA/DNA, RNA/DNA, or RNA/RNA hybrids can form.

Background descriptions of the use of nucleic acid hybridization to detect particular nucleic acid sequences are given in Kohne, U.S. Pat. No. 4,851,330 issued Jul. 25, 1989, and by Hogan et al., International Patent Application No. PCT/US87/03009, entitled "Nucleic Acid Probes for Detection and/or Quantitation of Non-Viral organisms," both references hereby incorporated by reference herein. Hogan et al., supra, describe methods for determining the presence of a non-viral organism or a group of non-vital organisms in a sample (e.g., sputum, urine, blood and tissue sections, food, soil and water).

*Mycoplasma pneumoniae* is a prokaryote in the taxonomic Mollicutes class. Mollicutes lack a bacterial cell wall and have a small genome size. They are considered some of the smallest of the free-living microorganisms. *Mycoplasma pneumoniae* is a primary pathogen of man that produces acute respiratory disease. It is the most common cause of atypical pneumonia and is responsible for 15-20% of all pneumonia cases.

DNA hybridization assay probes directed to genomic sequences for detecting *Mycoplasma pneumoniae* are mentioned by Hyman et al., *J. Clin. Microbiol.* 25:726–728 (1987), Buck et al., *J. Clin. Microbiol.* 30:3280–3283 (1992), and Bernet et al., *J. Clin. Microbiol.* 27:2492–2495 (1989). Probes directed to ribosomal RNA (rRNA) sequences of *Mycoplasma pneumoniae* are mentioned by Tilton (*Diagn. Microbiol. Infec. Dis.* 10:109–112 (1988), Yogev et al., *J. Clin. Microbiol.* 26:1198–1201, (1988), Gobel et al., *J. Gen Microbiol.* 133:1969–1974, (1987), Hogan et al., Supra, Zivin and Monahah, EPO 305145, Application No. 88307793.5, and Gobel and Stanbridge, EPO 250662, Application No. 86304919.3. Kai et al., *J. Med. Microbiol.* 38:166–170, (1993), van Kuppeveld et al., *Applied and Envir. Microbiol.* 58:2606–2615, (1992), van Kuppeveld et al., *Applied and Envir. Microbiol.* 59:655 (1993), and Jensen et al., *APMIS* 97:1046–1048 (1989), describe primers directed to 16S rRNA sequences of *M. pneumoniae*. Weisburg and Pelletier, EPO Application Number 92305126.2, Publication Number 0 576 743 A1 mention probes to *Mycoplasma pneumoniae*, or, optionally *Mycoplasma pneumoniae* and *Mycoplasma genitalium*, nucleic acid. None of the references mentioned herein are admitted to be prior art.

SUMMARY OF THE INVENTION

The present invention describes oligonucleotides targeted to *Mycoplasma pneumoniae* nucleic acid sequences which are particularly useful to aid in detecting *Mycoplasma pneumoniae*. The oligonucleotides can aid in detecting *Mycoplasma pneumoniae* in different ways such as by acting as hybridization assay probes, helper probes, and/or amplification primers. Hybridization assay probes can preferentially hybridize to a *Mycoplasma pneumoniae* nucleic acid target region to form a detectable duplex indicating the presence of *Mycoplasma pneumoniae*. Helper probes can hybridize to a *Mycoplasma pneumoniae* nucleic acid target region under stringent hybridization assay conditions and can be used to enhance the formation of a hybridization assay probe:target nucleic acid duplex. Amplification primers can hybridize to a *Mycoplasma pneumoniae* target region under amplification conditions and can be used as a primers in amplification reactions producing *Mycoplasma pneumoniae* nucleic acid.

Hybridization assay probes and helper probes contain a targeted nucleic acid region having a nucleotide sequence complementary, or substantially complementary to a target sequence. The hybridization assay probes may also have additional nucleotides outside of the targeted nucleic acid region which are complementary or not complementary to *Mycoplasma pneumoniae* nucleic acid. Hybridization assay probes are preferably 12–100 nucleotides in length and the targeted nucleic acid region is substantially similar to a nucleotide sequence perfectly complementary to a target sequence.

A substantially similar nucleotide sequence is a nucleotide sequence identical to, or having no more than a 20% nucleotide base difference excluding RNA or DNA equivalent nucleotides than an identified nucleotide sequence and which enables an oligonucleotide to preferentially hybridize to rRNA or rDNA of *Mycoplasma pneumoniae*, over rRNA or rDNA of one or more closely related organism. Organisms closely related to *Mycoplasma pneumoniae*, include *Mycoplasma genitalium*, *Mycoplasma orale*, *Mycoplasma buccale*, *Mycoplasma faucium*, and *Mycoplasma salivarium*. Preferential hybridization can occur under stringent hybridization assay conditions. In general, reducing the degree of complementarity of an oligonucleotide targeted region to its target sequence decreases the degree or rate of hybridization of the oligonucleotide to its target region. However, additional non-complementary nucleotide(s) may facilitate the ability of an oligonucleotide to discriminate against non-target organisms. In alternate embodiments substantially similar refers to a 10% difference and a 5% difference to a particular nucleotide sequence.

"RNA and DNA equivalents" refer to RNA and DNA molecules having the same complementary base pair hybridization properties. RNA and DNA equivalents have different sugar groups (i.e., ribose versus deoxyribose), and may differ by the presence of uracil in RNA and thymine in DNA. The difference between RNA and DNA equivalents do not contribute to differences in substantially corresponding nucleic acid sequences because the equivalents have the same degree of complementarity to a particular sequence.

*Mycoplasma genitalium* appears to be the most closely related Mycoplasma to *Mycoplasma pneumoniae* and has a very similar rRNA sequence to *Mycoplasma pneumoniae* rRNA. Because of the greater phylogenetic divergence occurring between more distant organisms, hybridization assay probes able to distinguish Mycoplasma pneumoniae from *Mycoplasma genitalium* also distinguish *Mycoplasma pneumoniae* from non-related microorganisms and preferably other more distantly related Mycoplasma. Thus, hybridization assay probes able to distinguish the presence of *Mycoplasma pneumoniae* from *Mycoplasma genitalium* are useful for detecting *Mycoplasma pneumoniae*.

Species of Mycoplasma found in humans include *Mycoplasma pneumoniae, Mycoplasma genitalium, Mycoplasma orale, Mycoplasma buccale, Mycoplasma faucium,* and *Mycoplasma salivarium*. Preferably, hybridization assay probes preferentially hybridize to *Mycoplasma pneumoniae* nucleic acid over one or more, more preferably all, nucleic acids present in microorganisms selected from the group consisting of *Mycoplasma genitalium, Mycoplasma orale, Mycoplasma buccale, Mycoplasma faucium* and *Mycoplasma salivarium*.

Thus, a first aspect of the present invention describes hybridization assay probes able to preferentially hybridize to a *Mycoplasma pneumoniae* target nucleic acid sequence region. The hybridization assay probes have a targeted nucleic acid sequence complementary to ribosomal RNA (rRNA) or DNA (rDNA) of *Mycoplasma pneumoniae* target sequence. The hybridization assay probes are at least 90 % complementary, preferably perfectly complementary, to at least a portion of the described target sequence region. The portion is at least 10 nucleotides in length and preferably at least 18 nucleotides in length.

By "preferentially hybridize" is meant that under stringent hybridization assay conditions, hybridization assay probes can hybridize to their target nucleic acids to form stable probe:target hybrids indicating the presence of the target nucleic acid and does not form a sufficient number of stable probe:non-target hybrids to indicate the presence of a closely related non-target nucleic acid. Thus, the probe hybridizes to target nucleic acid to a sufficiently greater extent than to non-target nucleic acid to enable one skilled in the art to accurately detect the presence of Mycoplasma pneumoniae and distinguish its presence from that of a closely related organism.

Preferential hybridization can be measured using techniques known in the art and described herein, such as in the examples provided below. Preferably, there is at least a 100 fold difference between target and non-target hybridization signals, more preferably at least a 1,000 fold difference, more preferably at least a 10,000 fold difference. Preferably, non-target hybridization signals are no more than background level.

A *Mycoplasma pneumoniae* "target nucleic acid sequence region" refers to a nucleic acid sequence present in *Mycoplasma pneumoniae* nucleic acid or a sequence complementary thereto, which is not present in a closely related Mycoplasma species nucleic acid. Nucleic acids having nucleotide sequences complementary to a target sequence may be generated by target amplification techniques such as polymerase chain reaction (PCR) or transcription mediated amplification (e.g., Kacian and Fultz, *Nucleic Acid Amplification Methods.*, EPO application number 90307503.4).

A related aspect describes hybridization assay probes 18–100 nucleotides in length which comprise, consist essentially of, consist of, or have a nucleotide sequence substantially similar to, the sequences (written 5' to 3'):

| | |
|---|---|
| (SEQ. ID. NO. 1) | CAGTCAAACT CTAGCCATTA CCTGCTAAAG TCATT, |
| (SEQ. ID. NO. 2) | CACACTCTAG ATTAATAGTT TCCAATGC, |
| (SEQ. ID. NO. 3) | CATGCGCTTC CTAATGGTTA GC, |
| (SEQ. ID. NO. 4) | GCTGTTTCCA ACTACCGGAT TGCTC, |
| (SEQ. ID. NO. 5) | CCTACAACCC CTATCTAATG ATAAGTTTGG, |
| (SEQ. ID. NO. 6) | GCTTCTTCTA TCGTTTTCAA GTCCAC, |
| (SEQ. ID. NO. 7) | CCTTTTGCGC GCTGCTTTCC, |
| (SEQ. ID. NO. 8) | CGTCTACCAC AAGATATAAA TCTTATCC, |
| (SEQ. ID. NO. 85) | CTCTAGCCAT TACCTGCTAA AGTC, | oligonucleotides complementary thereto (SEQ. ID. NOs. 21, 24, 27, 30, 33, 36, 39, 42, and 87), RNA equivalents having uracil substituted for thymine (SEQ. ID. NOs: 22, 25, 28, 31, 34, 37, 40, 43 and 88) and RNA equivalents of the oligonucleotides complementary thereto, having uracil substituted for thymine (SEQ. ID. NOs: 23, 26, 29, 32, 35, 8, 41, 44, and 89).

These probes are complementary to a target region present in rRNA and/or rDNA which varies between *Mycoplasma pneumoniae* and *Mycoplasma genitalium*. The probes can hybridize to *Mycoplasma pneumoniae* nucleic acid and distinguish *Mycoplasma pneumoniae* from a closely related Mycoplasma and are useful for detecting the presence of *Mycoplasma pneumoniae*. In a preferred embodiment, the probes may be used to determine the quantity of *Mycoplasma pneumoniae* present in a sample.

Another aspect describes helper oligonucleotides. The helper oligonucleotides can have a targeted region having a nucleotide sequence perfectly complementary to at least 10 contiguous nucleic acids present in a helper target nucleotide sequence selected from the group consisting of:

| | |
|---|---|
| SEQ ID NO: 53 | GGAUUGAAAA GUCUGGUGUU AAAGGCAGCU GC, |
| SEQ ID NO: 56 | AGUUUUGGAA UUUCAUGUGG AGCGGUGAAA UGCGUAG, |
| SEQ ID NO: 59 | CCGCCCGUCA AACUAUGAAA GCUGGUAAUA UUUAAAAACG UGUU, |

-continued

| | |
|---|---|
| SEQ ID NO: 63 | AAGGAUAGCA CCGGUGAUUG GAGUGAAGUC G, |
| SEQ ID NO: 66 | GGUGGUAAGA ACCUCAGAUC CGGAGAUUUC CGAAUG, |
| SEQ ID NO: 69 | GAUGAAUAAA UAGUCAUAUU AAAGCGAUAC GUG, |
| SEQ ID NO: 72 | CGUGUGUAGU GGCGAGCGAA AGCGGAACA, |
| SEQ ID NO: 75 | GUGAUAGCCC CGUAUUUGAA AUUGUUUUCA UACCUAGCGA G, |
| SEQ ID NO: 78 | GCGCCGAAGA UGUAACGGGG CUAAGUAUAU UACCGAAUUU AU, and |
| SEQ ID NO: 81 | AGCGUUGUAU UGGAGUUGAA GUCAAAGCGU GAGC. |

Helper probes can be used to facilitate hybridization of a hybridization assay probe to its target nucleic acid sequence. Helper probes facilitate hybridization by enhancing the kinetics and/or the $T_m$ of the target:hybridization probe duplex. Helper probes are generally described in Hogan and Milliman, U.S. Pat. No. 5,030,557, which is hereby incorporated by reference herein.

In preferred embodiments helper probes are oligonucleotides which have, consist essentially of, or consist of, the following nucleotide sequences (written 5'-3'):

| | |
|---|---|
| SEQ. ID. NO. 9 | CTTCCCAAAT AAATGAACTT TACAATCTTA AAGACCTTCA TCGTTCACGC GGC, |
| SEQ. ID. NO. 10 | CGCGACTGCT GGCACATAGT TAGTCGTCAC TTATTCAAAA TGGTA, |
| SEQ. ID. NO. 11 | GCAGCTGCCT TTAACACCAG ACTTTTCAAT CC, |
| SEQ. ID. NO. 12 | CTACGCATTT CACCGCTCCA CATGAAATTC CAAAACT, |
| SEQ. ID. NO. 13 | AACACGTTTT TAAATATTAC CAGCTTTCAT AGTTTGACGG GCGG, |
| SEQ. ID. NO. 14 | CGACTTCACT CCAATCACCG GTGCTATCCT T, |
| SEQ. ID. NO. 15 | CATTCGGAAA TCTCCGGATC TGAGGTTCTT ACCACC, |
| SEQ. ID. NO. 16 | CACGTATCGC TTTAATATGA CTATTTATTC ATC, |
| SEQ. ID. NO. 17 | TGTTCCGCTT TCGCTCGCCA CTACACACG, |
| SEQ. ID. NO. 18 | CTCGCTAGGT ATGAAAACAA TTTCAAATAC GGGGCTATCA C, |
| SEQ. ID. NO. 19 | ATAAATTCGG TAATATACTT AGCCCCGTTA CATCTTCGGC GC, |
| SEQ. ID. NO. 20 | GCTCACGCTT TGACTTCAAC TCCAATACAA CGCT; | and RNA equivalents thereto SEQ. ID. NOs. 46, 49, 52, 55, 58, 62, 65, 68, 71, 74, 77 and 80. The helper probe can hybridize to the same target nucleic acid as a hybridization assay probe and are preferably 12 to 100 nucleotide in length, more preferably 18 to 50 nucleotide in length.

Some oligonucleotides can be used alternatively as a hybridization assay probe or a helper probe. Examples of such oligonucleotides are those having the nucleotide sequence of SEQ. ID. Nos. 5, 6, or 7.

Another aspect of the present invention describe probe mixes for detecting *Mycoplasma pneumoniae* under stringent hybridization assay conditions. The probe mix contains a hybridization assay probe and at least one helper probe. In preferred embodiments, different hybridization assay probe and helper probe combinations are described.

Another aspect of the present invention describes compositions comprising a nucleic acid hybrid. The hybrid is made up of a hybridization assay probe and a nucleic acid molecule having a nucleic acid sequence substantially complementary thereto. One use of the formed hybrid is to detect the presence of a target sequence. For example, acridinium ester ("AE") present in hybrids is resistant to hydrolysis in alkali solution while acridinium ester present in single-stranded nucleic acid is hydrolyzed in alkali solution (Arnold et al., entitled "Homogeneous Protection Assay," EPO application number 88308767.8, publication number 309230, hereby incorporated by reference herein). Thus, binding of AE-labeled probe to target can be detected, after hydrolysis of the unbound AE-labeled probe, by measuring chemiluminescence of acridinium ester remaining in the nucleic acid hybrid.

In another aspect, the invention features amplification oligonucleotides useful for amplifying *Mycoplsma pneumoniae* target regions. Amplification oligonucleotides preferably have or consist essentially of the following nucleotide sequences:

| | |
|---|---|
| SEQ. ID. NO. 51: | GGATTGAAAA GTCTGGTGTT AAAGGCAGCT GC, |
| SEQ. ID. NO. 82: | CGCCACTGGT GTTCCTTCAT ATATCTACCC, |
| SEQ. ID. NO. 83: | ATCAAAGTTG AAAGGACCTG CAAGGGTTCG T, |
| SEQ. ID. NO. 84: | CTGCTGGCAC ATAGTTAGTC GTC; and |

RNA equivalents having uracil substituted for thymine, SEQ. ID. NOs. 53, 61, 90, and 91. Amplification oligonucleotides are preferably 12 to 100 nucleotides in length, more preferably 18 to 50.

Amplification oligonucleotides sequences may have modifications, such as blocked 3' and/or 5' termini or additions including, but not limited to, specific nucleic acid sequences recognized by an RNA polymerase, (e.g., the promoter sequence for T7, T3, or SP6 RNA polymerase); sequences enhancing initiation or elongation of RNA transcription by an RNA polymerase; or sequences providing for intramolecular base pairing and encouraging the formation of secondary or tertiary nucleic acid structures.

Amplification oligonucleotides can be used in nucleic acid amplification procedures, such as the polymerase chain reaction or an amplification reaction using RNA polymerase, DNA polymerase and RNase H or its equivalent, as described by Kacian and Fultz supra, and by Sninsky et al., U.S. Pat. No. 5,079,351; both references hereby incorporated by reference herein.

In other aspects, methods are described for using the hybridization assay probes, helper probes, and amplification oligonucleotides. These methods are particularly useful to test samples obtained from human specimens for the presence of Mycoplasma pneumoniae.

The oligonucleotides and their use described herein offer a rapid, objective method of identifying and quantitating the presence of specific rRNA sequences unique to *Mycoplasma pneumoniae* in a test sample.

Other features and advantages of the invention will be apparent from the following description of the preferred embodiments thereof and from the claims.

DESCRIPTION OF THE PREFERRED EMBODIMENTS

Target nucleotide sequences useful for designing hybridization assay probes, amplification oligonucleotides, and/or helper probes are described herein. Target nucleotide sequences for hybridization assay probes are present in Mycoplasma pneumoniae nucleic acids but not the nucleic acids of closely related organisms. The identification of the target sequences, in addition to being useful for designing probes to detect *Mycoplasma pneumoniae*, also provides a basis for designing oligonucleotides to inhibit the growth of Mycoplasma pneumoniae. For examples, oligonucleotides such as ribozymes and anti-sense oligonucleotides targeted to *Mycoplasma pneumoniae* nucleic acid needed for microbial growth should be able to inhibit activity of the nucleic acid, thereby inhibiting *Mycoplasma pneumoniae* growth. Such oligonucleotides can be used to therapeutically treat patients infected with *Mycoplasma pneumoniae.* A more detailed description of oligonucleotide anti-sense activity is provided in publications such as Helene, C. and Toulme, J. *Biochimica et Bioplysica Acta* 1049:99 (1990), and Uhlmann, E. and Peyman, A. *Chemical Reviews* 90:543 (1990).

I. DEFINITIONS

By "target nucleic acid" is meant a nucleic acid comprising a target nucleic acid sequence.

By "target nucleic acid sequence," "target nucleotide sequence" or "target sequence" is meant a specific deoxyribonucleotide or ribonucleotide sequence, or the nucleic acid sequence perfectly complementary thereto.

"Stringent" hybridization assay conditions refer to conditions wherein a hybridization assay probe preferentially hybridizes with target nucleic acid (preferably rRNA or rDNA of *Mycoplasma pneumoniae*) and not with nucleic acid derived from a closely related non-target microorganism. Stringent hybridization assay conditions may vary depending upon factors including the hybridization assay probe nucleotide sequence and length, closely related non-target sequences, and the target sequence. Hybridization conditions include the temperature and the composition of the hybridization reagents or solutions.

By "oligonucleotide" is meant two or more nucleotide subunits covalently joined together. The sugar groups of the nucleotide subunits may be ribose, deoxyribose, or modified derivatives thereof such as O-methyl ribose. The nucleotide subunits may by joined by linkages such as phosphodiester linkages, modified linkages or by non-nucleotide moieties, that do not prevent hybridization of the oligonucleotide to its complementary target nucleotide sequence. Modified linkages include those linkages in which a standard phosphodiester linkage is replaced with a different linkage, such as a phosphorothioate linkage, or methylphosphonate linkage.

By "probe" is meant an oligonucleotide having a nucleotide sequence sufficiently complementary to its target nucleic acid sequence to form a detectable hybrid oligonucleotide:target duplex under stringent hybridization assays conditions. A probe is an isolated nucleic acid. Probes may have additional nucleotides outside of the targeted region so long as such nucleotides do not prevent hybridization under stringent hybridization conditions, and in the case of hybridization assay probes do not prevent preferentially hybridization- Non-complementary sequence, such as a promotor sequence, a binding site for RNA transcription, a restriction endonuclease recognition site, or sequences which will confer a desired secondary or tertiary structure such as a catalytic active site can be used to facilitate detection and/or amplification. Oligonucleotide probes of a defined sequence may be produced by techniques known to those of ordinary skill in the art, such as by chemical synthesis, and by in vitro or in vivo expression from recombinant nucleic acid molecules. Probes are preferably 12 to 100 nucleotides in length, more preferably 18 to 50 nucleotides in length.

A "hybridization assay probe" is an isolated nucleic acid which can preferentially hybridize to a target *Mycoplasma Pneumoniae* 5S, 16S, or 23S rRNA, or to the corresponding ribosomal DNA ("rDNA") nucleic acid, or to a nucleic acid having a nucleotide sequence complementary to the target nucleic acid under stringent hybridization assay conditions. A hybridization assay probe is preferably labeled with a reporter group moiety such as a radioisotope, a fluorescent moiety, a chemiluminescent moiety, an enzyme, or a ligand, which can be used to detect or confirm probe hybridization to its target sequence. A hybridization assay probe is preferably between 12 and 100 nucleotides in length, more preferably between 18 and 50 nucleotides in length.

By "isolated nucleic acid" is meant an oligonucleotide or nucleic acid molecule which is present in a form not found in nature without human intervention (e.g., recombined with foreign nucleic acid, isolated, or purified to some extent).

By "nucleic acid hybrid" or "hybrid" is meant a stable nucleic acid structure comprising a double-stranded, hydrogen-bonded region, preferably 12 to 100 nucleotides in length, more preferably 18 to 50 nucleotides in length. The structure is sufficiently stable to be detected by means such as chemiluminescent or fluorescent light detection, autoradiography, or gel electrophoresis. Such hybrids include RNA:RNA, RNA:DNA, or DNA:DNA duplex molecules.

By "amplification oligonucleotide" is meant an isolated nucleic acid capable of hybridizing with a target nucleic acid and acting as a primer and/or a promoter for nucleic acid synthesis. The target nucleic acid strand is the template for nucleic acid synthesis. Promoters recognized by an RNA polymerase such as T7, T3 and SP6 RNA polymerase can be used for transcription-based amplification. An amplification oligonucleotide is preferably 12 to 100 nucleotides in length; more preferably 18 to 50 nucleotides in length.

By "nucleic acid amplification" or "target amplification" is meant increasing the number of nucleic acid molecules having at least one target nucleic acid sequence.

By "negative sense" is meant a nucleic acid molecule perfectly complementary to a reference (i.e., sense) nucleic acid molecule.

The phrases "consist essentially of" or "consisting essentially of" means that the oligonucleotide has a nucleotide sequence substantially similar to a specified nucleotide sequence and may be up to four additional nucleotides longer or have two deleted nucleotides. Thus, these phrases contain both a sequence length limitation and a sequence variation limitation. Any additions or deletions are non-material variations of the specified nucleotide sequence which do not prevent the oligonucleotide from having its claimed property, such as being able to preferentially hybridize under stringent hybridization assay conditions to its target nucleic acid over non-target nucleic acids. The oligonucleotide may contain a nucleotide sequence substantially similar to a specified nucleic acid sequence without any additions or deletions.

By "sufficiently complementary" or "substantially complementary" is meant nucleic acids having a sufficient amount of contiguous complementary nucleotides to form, under stringent hybridization assay conditions, a hybrid stable for detection.

II. Detection of *Mycoplasma pneumoniae*

We have identified preferred target nucleotide sequences for hybridization assay probes, helpers probes and amplification oligonucleotides in *Mycoplasma pneumoniae* rRNA or rDNA. The hybridization assay probes can detect *Mycoplasma pneumoniae* and preferably distinguish it from the known and presumably most closely related taxonomic or phylogenetic neighbors and more distantly related organisms. Helper probes can be used to facilitate the hybridization of a hybridization assay probe to its target nucleotide sequence region. Amplification oligonucleotide can act as primers and may be part of promoter-primer combinations (i.e., a primer having an attached promoter sequence) to amplify a *Mycoplasma pneumoniae* target sequence.

Prokaryotic organisms (excluding viruses) contain rDNA genes encoding 5S rRNA, 16S rRNA and 23S rRNA. Partial or full rRNA sequences of *Mycoplasma pneumoniae* and other members of the family Mycoplasmatacease were obtained by nucleic acid sequencing techniques known to those of ordinary skill in the art. These sequences were aligned based on regions of sequence homology. Sequence variations among species were then identified from the aligned sequences. These variable regions were then used as target sequences for hybridization assay probes.

The nucleic acid hybridization assay probes of the present invention can distinguish *Mycoplasma pneumoniae* from a closely related Mycoplamsa, preferably *Mycoplasma genitalium*, the nearest phylogenetic neighbor to *Mycoplasma pneumoniae*. In a preferred embodiment, hybridization assay probes can also distinguish *Mycoplasma pneumoniae* from other Mycoplasma, such as *Mycoplasma orale*, *Mycoplasma faucium*, *Mycoplasma buccale*, and *Mycoplasma salivarium*. These Mycoplasma have been isolated from humans.

Obtaining rRNA Sequences

Sequence information was obtained experimentally and from published information. (See, Weisburg et al., *J. Bacteriol* 171:6455 (1989).) Experimental information was obtained by isolating and sequencing rRNA from various organisms using standard techniques known in the art. More specifically, rRNA sequence information was obtained by first using oligonucleotide primers complementary to conserved regions which vary little between prokaryotic organisms. The primer was then extended using reverse transcriptase and deoxyribonucleotides to produce cDNA. The cDNA nucleic acid sequences were determined using the method of dideoxynucleotide chain termination. (E.g., Lane et al., *Proc. Natl. Acad. Sci. USA*, 82:6955 (1985).)

Probe Design And Hybridization Conditions

Hybridization assay probes and helper probes hybridize to their target sequence at stringent hybridization conditions. Hybridization assay probes are designed to preferentially hybridize to *Mycoplasma pneumoniae* nucleic acid and helper probes can aid in assay probe hybridization. Amplification oligonucleotides aid in the amplification of target sequences. Oligonucleotides acting as helper probes or amplification oligonucleotides do not need to be able to preferentially hybridize to *Mycoplasma pneumoniae* nucleic acid.

To facilitate the identification of nucleic acid sequences to be used in the design of probes, the nucleotide sequences from different organisms were first aligned to maximize homology. Within the rRNA molecule there is a close relationship between secondary structure (caused in part by intramolecular hydrogen bonding) and function. This fact imposes restrictions on evolutionary changes in the primary nucleotide sequence causing the secondary structure to be maintained. For example, if a base is changed in one "strand" of a double helix (due to intramolecular hydrogen bonding, both "strands" are part of the same rRNA molecule), a compensating substitution usually occurs in the primary sequence of the other "strand" in order to preserve complementarity (this is referred to as co-variance), and thus the necessary secondary structure. This allows two very different rRNA sequences to be aligned based both on the conserved primary sequence and also on the conserved secondary structure elements. Potential target sequences for the hybridization assay probes described herein were identified by noting variations in the homology of the aligned sequences.

The sequence evolution at each of the variable regions is mostly divergent. Because of the divergence, corresponding rRNA variable regions of more distant phylogenetic relatives of *Mycoplasma pneumoniae* show greater differences from *Mycoplasma pneumoniae* rRNA than do the rRNAs of phylogenetically closer relatives. We observed sufficient variation between *Mycoplasma pneumoniae* and its closest phylogenetic relative, *Mycoplasma genitalium*, to identify preferred target sites and design hybridization assay probes useful for distinguishing between the nucleic acids of these two organisms.

Preferential hybridization of hybridization assay probes to their target nucleic acids can be accomplished by choosing the appropriate hybridization assay conditions and proper probe design. The stability of the probe:target nucleic acid hybrid should be chosen to be compatible with the assay and washing conditions so that stable, detectable hybrids only form between nucleic acids having highly complementary sequences. Manipulation of one or more of the different assay parameters determines the exact sensitivity and specificity of a particular hybridization assay probe.

The following guidelines are useful for designing probes and determining specific stringent hybridization assay conditions. Probes should be designed to have an appropriate melting temperature ($T_m$). The appropriate $T_m$ can be obtained by varying the probe length and nucleotide composition (percentage of G+C versus A+T). The probe length and nucleotide composition should preferably be chosen to correspond to a $T_m$ about 2°–10° C. higher than the temperature at which the final assay will be performed.

In general, the optimal hybridization temperature for an oligonucleotide is approximately 5° C. below the melting temperature for a given duplex. Incubation at temperatures below the optimum temperature may allow mismatched base sequences to hybridize and can therefore decrease specificity. The longer the oligonucleotide, the more hydrogen bonding between base pairs and, in general, the higher the $T_m$. Increasing the percentage of G and C also increases the $T_m$ because G—C base pairs exhibit additional hydrogen bonding and therefore greater thermal stability than A—T base pairs. Such consideration are known in the art. (See, e.g., Chapter 11 of Sambrook, et al., supra.)

A preferred method to determine $T_m$ measures hybridization using a hybridization protection assay (HPA) according to Arnold et al., supra entitled "Homogeneous Protection Assay." $T_m$ can be measured using HPA in the following manner. Probe molecules are labeled with an acridinium ester. Probe:target hybrids are formed in a lithium succinate buffer (0.1 M lithium succinate buffer, pH 5.0, 2 mM EDTA, 2 mM EGTA, 10% (w/v) lithium lauryl sulfate) using an excess amount of target. Aliquots of the solution containing the nucleic acid hybrids are then diluted in the lithium succinate buffered solution and incubated for five minutes at various temperatures starting below that of the anticipated $T_m$ (typically 55° C.) and increasing in 2°–5° C. increments. This solution is then diluted with a mild alkaline borate buffer (0.15 M sodium tetraborate, pH 7.6, 5% (v/v) TRI- TON® X-100) and incubated at a lower temperature (for example 50° C.) for ten minutes.

Under these conditions the acridinium ester attached to the single-stranded probe is hydrolyzed, while the acridinium ester attached to hybridized probe is relatively protected from hydrolysis. Thus, the amount of acridinium ester remaining after hydrolysis treatment is proportional to the number of hybrid molecules. The remaining acridinium ester can be measured by monitoring the chemiluminescence produced from the remaining acridinium ester by adding hydrogen peroxide and alkali to the solution. Chemiluminescence can be measured in a luminometer (e.g., the Gen-Probe LEADER® I or LEADER® 50). The resulting data is plotted as percent of maximum signal (usually from the lowest temperature) versus temperature. The $T_m$ is defined as the temperature at which 50% of the maximum signal remains. In addition to the method above, $T_m$ may be determined by isotopic methods known to those skilled in the art (see e.g., Hogan et al., supra).

The $T_m$ for a given hybrid varies depending on the nature of the hybridization solution used. Factors such as the salt concentration, detergents, and other solutes can affect hybrid stability during thermal denaturation (see J. Sambrook, et al., supra). Conditions such as ionic strength and the temperature at which a probe will be allowed to hybridize to target should be taken into account in probe construction. The thermal stability of a hybrid nucleic acid increases with the ionic strength of the reaction mixture. On the other hand, chemical reagents which disrupt hydrogen bonds, such as formamide, urea, dimethyl sulfoxide and alcohols, can greatly reduce hybrid thermal stability.

To ensure specificity of a hybridization assay probe for its target, it is preferable to design probes which hybridize only with target nucleic acid under conditions of high stringency. Only highly complementary nucleic acid hybrids form under conditions of high stringency. Accordingly, the stringency of the assay conditions determines the amount of complementarity which should exist between two nucleic acid strands in order to form a hybrid. Stringency should be chosen to maximize the difference in stability between the probe:target hybrid and potential probe:non-target hybrids.

Proper specificity may be achieved by minimizing the length of the hybridization assay probe having perfect complementarity to sequences of non-target organisms, by avoiding G and C rich regions of complementarity to non-target nucleic acids, and by constructing the probe to contain as many destabilizing mismatches to non-target sequences as possible. Whether a probe is appropriate for detecting only a specific type of organism depends largely on the thermal stability difference between probe:target hybrids versus probe:nontarget hybrids. In designing probes, the differences in these $T_m$ values should be as large as possible (preferably 2° C.–5° C. or more).

The length of the target nucleic acid sequence region, and accordingly the length of the hybridization probe substantially complementary targeted region, can also be important. In some cases, there may be several nucleotide sequences from a particular target region, varying in location and length, which may be used to design probes with the desired hybridization characteristics. In other cases, one sequence may be significantly better with regard to specificity than another which differs from it merely by a single base. While it is possible for nucleic acids that are not perfectly complementary to hybridize, the longest stretch of perfectly complementary nucleotides generally determines hybrid stability.

Regions of rRNA known to form strong internal structures inhibitory to hybridization are less preferred target regions.

Likewise, probes with extensive self-complementarity should be avoided. If a strand is wholly or partially involved in an intramolecular or intermolecular hybrid it will be less able to participate in the formation of a new intermolecular probe:target hybrid. Ribosomal RNA molecules are known to form very stable intramolecular helices and secondary structures by hydrogen bonding. By designing a probe to a region of the target nucleic acid which remains substantially single-stranded under hybridization conditions the rate and extent of hybridization between probe and target may be increased.

A genomic rDNA target occurs naturally in a double-stranded form, as does the product of the polymerase chain reaction (PCR). These double-stranded targets require denaturation prior to hybridization. Appropriate denaturation and hybridization conditions are known in the art (e.g., E. M. Southern, J. Mol. Biol. 98:503 (1975)).

Example of specific stringent hybridization conditions for hybridization assay probes are provided in the examples described below. Additional sets of stringent hybridization conditions can be determined based on the present disclosure by those of ordinary skill in the art. (See e.g., Sambrook, et al., Molecular Cloning: A Laboratory Manual (Cold Springs Harbor Laboratory Press, 1989) at Chapter 11.)

Helper Probes

The rate of nucleic acid hybridization of an assay probe with its target nucleic acid is enhanced by using "Helper Probes" as described in Hogan and Milliman, U.S. Pat. No. 5,030,557. Helper probes are sufficiently complementary to their target nucleic acid sequence to form a helper probe-:target duplex under stringent hybridization assay conditions. The stringent hybridization assay conditions used with a given helper probe are determined by the conditions in which a hybridization assay probe is used to preferentially hybridize to its target sequence.

Regions of single stranded RNA and DNA can be involved in secondary and tertiary structures even under stringent hybridization assay conditions. Such structures can sterically inhibit, or even block hybridization of a hybridization assay probe to its target region. Hybridization of the helper probe alters the secondary and tertiary structure of the target nucleic acid, thereby rendering the hybridization assay probe target region more accessible. As a result helper probes enhance the kinetics and/or the $T_m$ of the target:hybridization probe duplex. Helper probes are generally selected to hybridize to nucleic acid sequences located near the hybridization assay probe target region.

Helper probes which can be used with the hybridization assay probes of the present invention are targeted to nucleic acid sequences provided by SEQ. ID. NOs: 33, 36, 39, 45, 48, 51, 54, 57, 60, 64, 67, 70, 73, 76 and 79. The probes are preferably 12 to 100 nucleotides in length and contain a targeted region of 10 nucleotides of which at least 9 out of the 10 nucleotides are perfectly complementary to a nucleic acid sequence present in the target region.

Examples of helper probes useful in the present invention are those having, consisting essentially of, or consisting of, the following nucleotide sequences (written 5' to 3'):

| | |
|---|---|
| (SEQ. ID. NO. 5) | CCTACAACCC CTATCTAATG ATAAGTTTGG |
| (SEQ. ID. NO. 6) | GCTTCTTCTA TCGTTTTCAA GTCCAC, |
| (SEQ. ID. NO. 7) | CCTTTTGCGC GCTGCTTTCC, |
| (SEQ. ID. NO. 9) | CTTCCCAAAT AAATGAACTT TACAATCTTA AAGACCTTCA TCGTTCACGC GGC, |
| (SEQ. ID. NO. 10) | CGCGACTGCT GGCACATAGT TAGTCGTCAC |

-continued

| | |
|---|---|
| | TTATTCAAAA TGGTA, |
| (SEQ. ID. NO. 11) | GCAGCTGCCT TTAACACCAG ACTTTTCAAT CC, |
| (SEQ. ID. NO. 12) | CTACGCATTT CACCGCTCCA CATGAAATTC CAAAACT, |
| (SEQ. ID. NO. 13) | AACACGTTTT TAAATATTAC CAGCTTTCAT AGTTTGACGG GCGG, |
| (SEQ. ID. NO. 14) | CGACTTCACT CCAATCACCG GTGCTATCCT T, |
| (SEQ. ID. NO. 15) | CATTCGGAAA TCTCCGGATC TGAGGTTCTT ACCACC, |
| (SEQ. ID. NO. 16) | CACGTATCGC TTTAATATGA CTATTTATTC ATC, |
| (SEQ. ID. NO. 17) | TGTTCCGCTT TCGCTCGCCA CTACACACG, |
| (SEQ. ID. NO. 18) | CTCGCTAGGT ATGAAAACAA TTTCAAATAC GGGGCTATCA C, |
| (SEQ. ID. NO. 19) | ATAAATTCGG TAATATACTT AGCCCCGTTA CATCTTCGGC GC, |
| (SEQ. ID. NO. 20) | GCTCACGCTT TGACTTCAAC TCCAATACAA CGCT; | and RNA equivalents thereto, SEQ. ID. NOs: 34, 37, 40, 46, 9, 52, 55, 58, 62, 65, 68, 71, 74, 77 and 80.

Preferably, the following hybridization assay probe and helper probes combinations are used:

TABLE 1

| Hybridization Probe (SEQ. ID. NO.) | Helper Probes (SE0. ID. NO.) |
|---|---|
| 1 | 9 and 10 |
| 2 | 11 and 12 |
| 3 | 13 and 14 |
| 4 | 15 and 16 |
| 5 | 17 and 6 |
| 6 | 5 and 7 |
| 7 | 6 and 18 |
| 8 | 19 and 20 |
| 85 | 9 and 10 |

Amplification oligonucleotides

The degree of amplification observed with a set of primers or promoter-primers depends on several factors, including the ability of the oligonucleotides to hybridize to their specific target sequences and their ability to be extended or be recognized by an RNA polymerase. While oligonucleotides of different lengths and base composition may be used, more preferred amplification oligonucleotides have target binding regions of 18–50 bases and a predicted hybrid $T_m$ of about 65° C.

A target nucleic acid sequence present on a nucleic acid molecule can be amplified using an amplification oligonucleotide 5' of the target sequence and an amplification oligonucleotide 3' of the target sequence. The preferred target sites for amplification oligonucleotides are regions greater than about 15 bases in length. The amplified region, defined by the amplification oligonucleotides, is preferably about 350 bases, and more preferably within 150 bases.

Parameters affecting probe hybridization such as $T_m$, complementarity and secondary structure also affect primer hybridization and therefore performance of the amplification oligonucleotides. These considerations, which were discussed above in the section concerning probe design, can be modified depending upon the amplification conditions. For example, amplification can be carried under conditions of lower stringency then diagnostic hybridization assay conditions.

The degree of non-specific extension (primer-dimer or non-target copying) can affect amplification efficiency. Primers are preferably selected to have low self- or cross-complementarity, particularly at the 3' ends of the sequence. Long homopolymer tracts and high GC content are preferably avoided to reduce spurious primer extension. Computer programs are commercially available to aid in this aspect of the design.

III. OLIGONUCLEOTIDE SYNTHESIS

Defined oligonucleotide may be produced by any of several well-known methods, including automated solid-phase chemical synthesis using cyanoethylphosphoramidite precursors (Barone et al., *Nucleic Acids Research* 12:4051 (1984)), and as described in Sambrook, et al., supra, at ch. 11. Following synthesis and purification of an oligonucleotide, several different procedures may be utilized to determine the acceptability of the oligonucleotide in terms of size and purity. Such procedures include polyacrylamide gel electrophoresis and High Pressure Liquid Chromatography.

Hybridization assay probes may be labeled with a reporter group by any of several well-known methods (J. Sambroock, et al., e.g., supra). Useful labels include radioisotopes and non-radioactive reporting groups. Isotopic labels include $^3H$, $^{35}S$, $^{32}P$, $^{125}I$, $^{57}Co$ and $^{14}C$. isotopic labels can be introduced into an oligonucleotide by techniques known in the art such as nick translation, end labeling, second strand synthesis, reverse transcription, and by chemical methods. When using radiolabeled probes, hybridization can be detected by techniques such as autoradiography, scintillation counting, or gamma counting. The chosen detection method depends on the particular radioisotope used for labeling.

Non-isotopic materials can also be used for labeling and may be introduced internally between nucleotides or at an end of the oligonucleotide. Modified nucleotides may be incorporated enzymatically or chemically. Chemical modifications of the oligonucleotide may be performed during or after synthesis of the oligonucleotide using techniques known in the art. For example, through the use of non-nucleotide linker groups as described by Arnold et al., entitled "Non-Nucleotide Linking Reagents for Nucleotide Probes," EPO application number 88308766.0, publication number 313219, hereby incorporated by reference herein. Non-isotopic labels include fluorescent molecules, chemiluminescent molecules, enzymes, cofactors, enzyme substrates, and haptens or other ligands.

Preferably, the hybridization assay probes are labeled with an acridinium ester. Acridinium ester labeling may be performed as described by Arnold et al., U.S. Pat. No. 5,185,439 entitled "Acridinium Ester Labeling and Purification of Nucleotide Probes" issued Feb. 9, 1993 and hereby incorporated by reference herein.

IV. EXAMPLES

Examples are provided below illustrating different aspects and embodiments of the present invention. The examples illustrate methodology by which oligonucleotides having, consisting essentially of, and substantially similar to, a specified nucleotide sequence of a hybridization assay probe, helper probe, or amplification oligonucleotide, can be obtained. These examples are not intended in any way to limit the disclosed invention.

Probes specific for *Mycoplasma pneumoniae* were designed by first sequencing prospective target areas using primers complementary to the rRNAs of *Mycoplasma pneumoniae* (ATCC NO. 15531) and *Mycoplasma genitalium* (ATCC NO. 33530), or from published 16S sequences. These sequences were compared to determine variable regions. The rRNA sequences of phylogenetically near neighbors, including *Mycoplasma hyopneumoniae, Mycoplasma arginini, Mycoplasma liphophilum, Mycoplasma californicum, Mycoplasma bovigenitalium, Mycoplasma salivarium, Mycoplasma hominis, Mycoplasma arthritidis, Mycoplasma arginini, Mycoplasma pulmonis, Mycoplasma mycoides, Mycoplasma imitans, Mycoplasma iowae, Mycoplasma muris, Mycoplasma pirum, Mycoplasma gallisepticum*, and *U. urealyticum* were also compared to *Mycoplasma pneumoniae* rRNA to determine variable regions.

Hybridization assay probes having the following nucleotide sequences are featured in the examples described below:

| | |
|---|---|
| (SEQ. ID. NO. 1) | CAGTCAAACT CTAGCCATTA CCTGCTAAAG TCATT, |
| (SEQ. ID. NO. 2) | CACACTCTAG ATTAATAGTT TCCAATGC, |
| (SEQ. ID. NO. 3) | CATGCGCTTC CTAATGGTTA GC, |
| (SEQ. ID. NO. 4) | GCTGTTTCCA ACTACCGGAT TGCTC, |
| (SEQ. ID. NO. 5) | CCTACAACCC CTATCTAATG ATAAGTTTGG, |
| (SEQ. ID. NO. 6) | GCTTCTTCTA TCGTTTTCAA GTCCAC, |
| (SEQ. ID. NO. 7) | CCTTTTGCGC GCTGCTTTCC, |
| (SEQ. ID. NO. 8) | CGTCTACCAC AAGATATAAA TCTTATCC, |
| (SEQ. ID. NO. 24) | GCATTGGAAA CTATTAATCT AGAGTGTG, and |
| (SEQ. ID. NO. 85) | CTCTAGCCAT TACCTGCTAA AGTC. |

The probes were synthesized with a non-nucleotide linker as described by Arnold et al., "on-Nucleotide Linking Reagents For Nucleotide Probes," supra, then labeled with a chemiluminescent acridinium ester as described by Arnold et al., U.S. Pat. No. 5,185,439. The reactivity and specificity of the probes for *Mycoplasma pneumoniae* nucleic acid were demonstrated using a two phase hybridization and separation format (the results shown in Tables 3, 4 and 5) or a single phase homogeneous assay format (the results shown in Tables 2, 6 and 7). These procedures are described by Arnold et al., "Homogeneous neous Protection Assay", supra; Arnold et al., "Polycationic Supports and Nucleic Acid Purification, Separation and Hybridization", EPO Publication No. 0 281 390, and Arnold et al., *Clin. Chem.*, 35:1588 (1989), all of which are hereby incorporated by reference herein.

Results are given in relative light units (RLU), a measure of the photons detected by the luminometer. Probes were hybridized to a nucleic acid in a cell lysate, or purified RNA. Purified RNA was obtained as generally described in J. Sambrook, et al., supra. Lysates, especially of Mycobacteria, Gram positive organisms, or yeasts, can be obtained as described by Murphy et al., "Method for Releasing RNA and DNA from Cells," EPO Publication No. 288618, hereby incorporated by reference herein. The following examples describe hybridization assay probes targeted to *Mycoplasma pneumoniae* rRNA sequences, or the corresponding gene, and their use in a hybridization assay.

Example 1: Hybridization to *Mycoplasma Pneumoniae* Nucleic Acid Versus *Mycoplasma genitalium* Nucleic Acid Hybridization of individual acridinium ester-labeled probes to *Mycoplasma pneumoniae* and *Mycoplasma genitalium* rRNA was evaluated. Purified RNA (50 ng) was hybridized to probe mixes in 100 ml 0.05 M lithium succinate pH 5, 0.6 M LiCl, 1% (w/v) lithium lauryl sulfate, 10 mM EDTA, 10 mM EGTA at 60° C. for 30 minutes, followed by addition of 300 µl of 0.15 M sodium tetraborate pH 8.5, 1% TRITON®X-100 at 60° C. for 8–9 minutes. Each sample was tested in duplicate with 0.16 pmol hybridization assay probe and 0.4 pmol helper probe. Acridinium ester signal production was read in a luminometer by injecting 0.1% hydrogen peroxide in 1 mM nitric acid, followed by injection of a 1 N sodium hydroxide solution.

As shown in Table 2, probes targeted to *Mycoplasma pneumoniae* nucleic acid readily distinguish *Mycoplasma pneumoniae* from *Mycoplasma genitalium*. The data in this table are reported in RLU without subtracting background or negative control values. The results of duplicate experiments are reported. An acridinium ester-labeled probe having the nucleotide sequence provided by SEQ. ID. NO. 1 was used with unlabeled helper probes having the nucleotide sequences of SEQ. ID. NOs. 9 and 10. An acridinium ester-labeled probe having the nucleotide sequence of SEQ. ID. NO. 2 was used with unlabeled helper probes having the nucleotide sequences of SEQ. ID. NOs. 11 and 12. An acridinium ester-labeled probe having the nucleotide sequence of SEQ. ID. NO. 3 was used with unlabeled helper probes having the nucleotide sequences of SEQ. ID. NOs. 13 and 14. An acridinium ester-labeled probe having the nucleotide sequence of SEQ. ID. NO. 4 was used with unlabeled helper probes having the nucleotide sequences of SEQ. ID. NOs. 15 and 16. An acridinium ester-labeled probe having the nucleotide sequence of SEQ. ID. NO. 5 was used with unlabeled helper probe having the nucleotide sequence of SEQ. ID. NO. 17. An acridinium ester-labeled probe having the nucleotide sequence of SEQ. ID. NO. 6 was used without helper probes. An acridinium ester-labeled probe having the nucleotide sequence of SEQ. ID. NO. 7 was used with unlabeled helper probe having the nucleotide sequence of SEQ. ID. NO. 18. An acridinium ester-labeled probe having the nucleotide sequence of SEQ. ID. NO. 8 was used with unlabeled helper probes having the nucleotide sequences of SEQ. ID. NOs. 19 and 20.

TABLE 2

HYBRIDIZATION OF INDIVIDUAL PROBES TO *MYCOPLASMA PNEUMONIAE* AND *MYCOPLASMA GENITALIUM*

| | Relative Light Units (RLU) | | |
|---|---|---|---|
| SEQ. ID. NO. (Probe) | *M. pneumoniae* (Target) | *M. genitalium* (Target) | No target |
| 1 | 504,267 | 10,696 | 1,591 |
|   | 528,973 | 10,322 | 1,609 |
| 2 | 973,978 | 1,031 | 1,116 |
|   | 966,475 | 1,070 | 1,001 |
| 3 | 441,328 | 5,022 | 5,524 |
|   | 458,071 | 5,080 | 5,396 |
| 4 | 768,216 | 6,065 | 6,103 |
|   | 734,084 | 6,152 | 6,426 |
| 5 | 698,120 | 1,296 | 1,714 |
|   | 772,121 | 1,628 | 1,757 |
| 6 | 406,552 | 1,682 | 1,608 |
|   | 422,001 | 1,519 | 1,595 |
| 7 | 806,302 | 1,375 | 1,373 |
|   | 791,519 | 1,338 | 1,520 |

TABLE 2-continued

HYBRIDIZATION OF INDIVIDUAL PROBES TO MYCOPLASMA PNEUMONIAE AND MYCOPLASMA GENITALIUM

| | Relative Light Units (RLU) | | |
|---|---|---|---|
| SEQ. ID. NO. (Probe) | M. pneumoniae (Target) | M. genitalium (Target) | No target |
| 8 | 569,196 | 10,343 | 7,520 |
| | 578,800 | 10,457 | 7,749 |

The data indicate that each probe reacted well with *Mycoplasma pneumoniae* target rRNA. Probes 2, 3, 4, 5, 6, and 7 showed no significant reaction over background signal with *Mycoplasma genitalium* target. The probe mix containing a probe having the nucleotide sequence of SEQ. ID. NO. 8, and the probe mix containing a probe having the nucleotide sequence of SEQ. ID. NO. 1, showed a slight signal over background when combined with 50 ng of *Mycoplasma genitalium* rRNA under these assay conditions. This amount of purified rRNA corresponds to about $2 \times 10^{10}$ copies of rRNA, or approximately 20 million bacteria.

Example 2: Preferential Hybridization to *Mycoplasma Pneumoniae* Nucleic Acid

This example illustrates the ability of a probe mixture containing acridinium ester-labeled probes targeted to *Mycoplasma pneumoniae* rRNA to detect various *Mycoplasma pneumoniae* strains but not other microorganisms in a hybridization and separation assay format. This format gives lower background signals than the homogeneous assay format described above and used to obtain the data shown in Table 2. The probe mixture contained acridinium ester-labeled probes having the following nucleotide sequences:

| | |
|---|---|
| (SEQ. ID. NO. 1) | CAGTCAAACT CTAGCCATTA CCTGCTAAAG TCATT, |
| (SEQ. ID. NO. 2) | CACACTCTAG ATTAATAGTT TCCAATGC, |
| (SEQ. ID. NO. 3) | CATGCGCTTC CTAATGGTTA GC, |
| (SEQ. ID. NO. 4) | GCTGTTTCCA ACTACCGGAT TGCTC, |
| (SEQ. ID. NO. 5) | CCTACAACCC CTATCTAATG ATAAGTTTGG, |
| (SEQ. ID. NO. 6) | GCTTCTTCTA TCGTTTTCAA GTCCAC, |
| (SEQ. ID. NO. 7) | CCTTTTGCGC GCTGCTTTCC, |
| (SEQ. ID. NO. 8) | CGTCTACCAC AAGATATAAA TCTTATCC, | and unlabeled helper probes (SEQ. ID. NOs. 9, 10, 11, 12, 13, 14, 15, 16, 17, 18, 19 and 20).

Table 3 presents data obtained using the probe mix against an excess of RNA released from liquid broth cultures containing $10^6$–$10^8$ organisms. For each sample, hybridization solution containing 0.19 M lithium succinate pH 5, 0.62 M lithium lauryl sulfate, 3 mMEDTA, 3 mMEGTA, and the probe mix was combined with an equal volume of cell lysate (about 100 ng of rRNA) and incubated at 60° C. for one hour. Hybrids were then bound to magnetic amine microspheres (Perseptive Biosystems, Inc., Cambridge, MA) in a solution containing 0.19 M sodium tetraborate pH 7.5, 6% (v/v) TRITON®X-100 and washed once in a solution containing 20 mM sodium tetraborate pH 10.4. The particle-associated chemiluminescence from the hybridized acridinium ester-labeled probes was measured in a luminometer as described in Example 1. The data in Table 3 show that the probe mix indicates the presence of *Mycoplasma pneumoniae* and distinguishes Mycoplasma pneumoniae from several closely related Mycoplasma, Acholeplasma, Ureaplasma and Spiroplasma species.

An all-bacteria/yeast probe mixture was used as a positive control to demonstrate the presence of bacterial nucleic acid (data not shown). Hogan et al., "Nucleic Acid Probes for Detection and/or Quantitation of Non-vital Organisms, supra, gives examples of suitable all-bacteria/yeast probe mixtures.

TABLE 3

HYBRIDIZATION OF *MYCOPLASMA PNEUMONIAE* 16S AND 23S rRNA PROBES TO MYCOPLASMA SPECIES

| Organism[1] | ATCC or ID No.[2] | Net RLU |
|---|---|---|
| Acholeplasma axanthum | 27378 | −17 |
| Acholeplasma laidlawii | 29804 | 9 |
| Mycoplasma arginini | 23838 | 2 |
| Mycoplasma arthritidis | 35943 | −5 |
| Mycoplasma bovigenitalium | 19852 | 0 |
| Mycoplasma bovis | 25523 | −7 |
| Mycoplasma buccale | 23636 | −21 |
| Mycoplasma californicum | 33461 | 75 |
| Mycoplasma capricolum | 23205 | −18 |
| Mycoplasma columbinasale | 33549 | 97 |
| Mycoplasma columborale | 29258 | −9 |
| Mycoplasma faucium | 25293 | 0 |
| Mycoplasma fermentans | 15474 | −13 |
| Mycoplasma fermentans | 19989 | −34 |
| Mycoplasma gallisepticum | 19610 | 965 |
| Mycoplasma gallopavonis | 33551 | 137 |
| Mycoplasma genitalium | 33530 | −5 |
| Mycoplasma genitalium | 49123 | 10,008 |
| Mycoplasma genitalium | CI-4594 | 12,333 |
| Mycoplasma genitalium | CI-4595 | 14,673 |
| Mycoplasma hominis | 23114 | −7 |
| Mycoplasma hominis | 15056 | 29 |
| Mycoplasma hominis | 27545 | 91 |
| Mycoplasma hominis | 43518 | 8 |
| Mycoplasma hominis | 43519 | 27 |
| Mycoplasma hominis | 43520 | 8 |
| Mycoplasma hominis | 43521 | 39 |
| Mycoplasma hominis | 43522 | 41 |
| Mycoplasma hominis | 43523 | 36 |
| Mycoplasma hyorhinis | 17981 | −19 |
| Mycoplasma hypopneumoniae | 27719 | −20 |
| Mycoplasma iowae | 33552 | 238 |
| Mycoplasma muris | 33757 | 70 |
| Mycoplasma neurolyticum | 19988 | 55 |
| Mycoplasma orale | 23714 | −4 |
| Mycoplasma orale | 15544 | −16 |
| Mycoplasma pirum | 25960 | 383 |
| Mycoplasma pneumoniae | 15531 | 942,820 |
| Mycoplasma pneumoniae | 15492 | 970,484 |
| Mycoplasma pneumoniae | 15293 | 799,771 |
| Mycoplasma pneumoniae | 15377 | 951,643 |
| Mycoplasma pneumoniae | 29085 | 797,976 |
| Mycoplasma pneumoniae | 29342 | 973,261 |
| Mycoplasma pneumoniae | 29343 | 899,546 |
| Mycoplasma primatum | 15497 | −9 |
| Mycoplasma salivarium | 23064 | −1 |
| Mycoplasma salivarium | 14277 | −6 |
| Mycoplasma salivarium | 23557 | −10 |
| Mycoplasma salivarium | 29803 | −9 |
| Mycoplasma salivarium | 33130 | −12 |
| Spiroplasma mirum | 29335 | 57 |
| Ureaplasma urealyticum | 27815 | 90 |
| Ureaplasma urealyticum | 27817 | 117 |
| Ureaplasma urealyticum | 27818 | 173 |
| Ureaplasma urealyticum | 27819 | 138 |
| Ureaplasma urealyticum | 29558 | 147 |

[1]Approximately 100 ng of RNA were assayed.
[2]Non-ATCC ID Numbers have a CI prefix.

Chemiluminescence was measured in a Gen-Probe LEADER® I luminometer and data are expressed in net Relative Light Units (signal minus the value obtained with a sample containing 1 ng of non-Mycoplasma rRNA). The probe mix exhibited a low level of cross-reactivity to some Mycoplasma isolates.

Example 3: Determining Extent of Cross-reactivity

To determine the extent of cross-reactivity, decreasing amounts of RNA were assayed to determine the amount of RNA necessary to give a net signal of greater than or equal to 300 RLU, a possible cutoff value in the hybridization and separation assay format. Results are shown in Table 4 using the Example 2 probe mix and protocol.

TABLE 4

HYBRIDIZATION OF 16s AARD 23s rRNA PROBES TO MYCOPLASMA SPECIES

| Species | ATCC or ID No. | Amount of RNA Necessary for a Positive Signal (>300 RLU) |
|---|---|---|
| M. genitalium | 49123 | 2.3 ng |
| M. genitalium | CI-4594 | 1.9 ng |
| M. genitalium | CI-4595 | 1.7 ng |
| M. gallisepticum | 19610 | >10 ng |
| M. pirum | 25960 | >10 ng |

Relative to its reactivity with *Mycoplasma pneumoniae* RNA, the probe mix showed low reactivity to these five isolates. Greater than 10 ng of Mycoplasma these five isolates. Greater than 10 ng of *Mycoplasma gallisepticum* and *Mycoplasma pirum* RNA were required to give a positive result. Although the cross-reactivities of three *Mycoplasma genitalium* RNA's were somewhat higher, there was still a 400-fold difference in reactivity between *Mycoplasma pneumoniae* rRNA and *Mycoplasma genitalium* rRNA. Cross-reactivity in clinical specimens is not expected to be detectable above background.

Example 4: Preferential Probe Hybridization

Table 5 shows that the probe mix, described in Example 2, distinguishes *Mycoplasma pneumoniae* from twenty-seven bacterial genera representing a phylogenetic cross section of microorganisms using the assay format described in Example 2. An all-bacteria/yeast probe mixture used as a control in this experiment indicated the presence of bacteria (data not shown).

TABLE 5

HYBRIDIZATION OF *MYCOPLASMA PNEUMONIAE* 16S AND 23S rRNA PROBES TO A PHYLOGENETIC CROSS SECTION.

| Organism[1] | ATCC No. | Net RLU[2] |
|---|---|---|
| Acinetobacter calcoaceticus | 33604 | 162 |
| Acinetobacter lwoffii | 15309 | 4 |
| Actinomyces israelii | 10049 | 153 |
| Actinomyces pyogenes | 19411 | 13 |
| Aerococcus viridans | 11563 | 9 |
| Aeromonas hydrophila | 7966 | −10 |
| Alcaligenes denitrificans | 27061 | 81 |
| Alcaligenes faecalis | 8750 | 92 |
| Bacillus subtilis | 6051 | 3 |
| Bacteroides fragilis | 23745 | 57 |
| Bordetella bronchiseptica | 10580 | 32 |
| Branhamella catarrhalis | 25238 | 20 |
| Brevibacterium linens | 9172 | 37 |
| Campylobacter jejuni | 33560 | 90 |
| Candida albicans | 18804 | 9 |
| Capnocytophaga ochracea | 27872 | 38 |
| Chromobacterium violaceum | 29094 | −7 |
| Clostridium innocuum | 14501 | 31 |
| Clostridium pasteurianum | 6013 | 75 |
| Clostridium perfringens | 13124 | 97 |
| Clostridium ramosum | 25582 | 59 |
| Corynebacterium diphtheriae | 11913 | 129 |
| Corynebacterium haemolyticum | 9345 | 59 |
| C. pseudodiphtheriticum | 10700 | 34 |
| C. pseudotuberculosis | 19410 | 39 |
| Corynebacterium xerosis | 373 | 14 |
| Cryptococcus neoformans | 32045 | 29 |

TABLE 5-continued

HYBRIDIZATION OF *MYCOPLASMA PNEUMONIAE* 16S AND 23S rRNA PROBES TO A PHYLOGENETIC CROSS SECTION.

| Organism[1] | ATCC No. | Net RLU[2] |
|---|---|---|
| Deinococcus radiodurans | 35073 | −9 |
| Dermatophilus congolensis | 14637 | 8 |
| Derxia gummosa | 15994 | 42 |
| Enterococcus faecalis | 19433 | 46 |
| Erysipelothrix rhusiopathiae | 19414 | 4 |
| Escherichia coli | 10798 | 15 |
| Flavobacterium meningosepticum | 13253 | 44 |
| Gemella haemolysans | 10379 | 31 |
| Haemophilus influenzae | 19418 | 1 |
| Klebsiella pneumoniae | 23357 | −1 |
| Lactobacillus acidophilus | 4356 | 39 |
| Lactococcus lactis cremoris | 19257 | 24 |
| Legionella pneumophila | 33152 | 61 |
| Leuconostoc paramesenteroides | 33313 | 54 |
| Listeria monocytogenes | 35152 | 44 |
| Micrococcus kristinae | 27570 | 13 |
| Micrococcus luteus | 4698 | −1 |
| Moraxella osloensis | 19976 | 20 |
| Mycobacterium gordonae | 14470 | −21 |
| Mycobacterium tuberculosis | 25177 | −9 |
| Neisseria lactamica | 23970 | 46 |
| Neisseria mucosa | 19696 | 10 |
| Neisseria sicca | 29193 | 12 |
| Nocardia asteroides | 19247 | 19 |
| Oerskovia turbata | 33225 | 3 |
| Oerskovia xanthineolytica | 27402 | 63 |
| Paracoccus dinitrificans | 17741 | 4 |
| Pediococcus acidilactici | 33314 | 21 |
| Peptostreptococcus magnus | 14955 | 56 |
| Peptostreptococcus anaerobius | 27337 | 34 |
| Propionibacterium acnes | 6919 | 9 |
| Proteus mirabilis | 25933 | 16 |
| Pseudomonas aeruginosa | 25330 | 8 |
| Rhodococcus bronchialis | 25592 | 15 |
| Rhodospirillum rubrum | 11170 | 31 |
| Staphylococcus aureus | 25923 | 20 |
| Staphylococcus aureus | 12598 | 16 |
| Staphylococcus aureus | 33591 | 10 |
| Staphylococcus epidermidis | 12228 | −4 |
| Streptococcus agalactiae | 13813 | 1 |
| Streptococcus mitis | 9811 | −5 |
| Streptococcus pneumoniae | 6303 | 5 |
| Streptococcus pyogenes | 19615 | −15 |
| Streptococcus sanguis | 10556 | −11 |
| Streptomyces griseus | 23345 | −13 |
| Vibrio parahaemolyticus | 17802 | −13 |
| Yersinia enterocolitica | 9610 | 3 |

[1]Greater than $10^7$ cells were assayed.
[2]Experimental value - the value obtained with 1 ng of non-Mycoplasma rRNA.

Example 5: Detection of Amplified Target

This example illustrates the use of *Mycoplasma pneumoniae* hybridization assay probes to detect the products of nucleic acid amplification. In this example, a *Mycoplasma pneumoniae* hybridization assay probe of the same sense as the target rRNA nucleic acid was used to detect the products of target nucleic acid amplification. *Mycoplasma pneumoniae* and *Mycoplasma genitalium* rRNA was separately amplified with primer having the nucleotide sequences of SEQ. ID. NO. 51 and a promoter-primer having the nucleotide sequences of SEQ. ID. NO. 82 containing the promoter sequence 5'-AATTTAATACGACTCACTATAGGGAGA-3' (SEQ. ID. NO. 92) at the 5' end. Amplification was performed using a Perkin-Elmer thermocycler as follows: the target nucleic acid was heated to 95° C. for 15 minutes, cooled to 42° C. in 100 µl of a solution containing 0.3 µM of the promoter-primer, 0.3 µM of primer, 50mMTris-HCl, pH 7.6, 25 mM KCl, 17.5 mM $MgCl_2$, 20 mMN-acetyl cysteine, 2.5 mM rATP, 2.5 mM rCTP, 2.5 mM rGTP, 2.5 mM rUTP, 1 mM dATP, 1 mM dCTP, 1 mM dGTP and 1 mM dTTP. Nine hundred units of MMLV reverse transcriptase and 400 U T7 RNA polymerase were added to each reaction and mixed. See Kacian et al., Nucleic Acid Sequence Amplification Method, Composition, and Kit, supra. Following a two hour incubation at 42° C., each entire reaction mixture was subjected to a hybridization assay using 0.12 pmol of an acridinium ester-labeled probe of the same sense as the target rRNA (SEQ. ID. NO. 24) using conditions described in Example 1. Results for each target nucleic acid are the average of five replicate reactions.

TABLE 6

HYBRIDIZATION OF "SAME-SENSE" *M. PNEUMONIAE*-SPECIFIC ASSAY PROBES TO NUCLEIC ACID AMPLIFICATION PRODUCTS

| Target Organism | Amount of target RNA | RLU |
|---|---|---|
| M. pneumoniae | 500 fg | 2,174,706 |
| M. pneumoniae | 50 fg | 780,001 |
| M. pneumoniae | 10 fg | 228,312 |
| M. genitalium | 500 fg | 1,642 |
| M. genitalium | 50 fg | 1,930 |
| M. genitalium | 10 fg | 1,990 |
| No added target | — | 1,383 | and specificity of hybridization assay probes targeted to nucleic acid sequences complementary to *Mycoplasma pneumoniae* rRNA to detect the product from a target amplification procedure.

Example 6: Detection of Amplified Target

This example also illustrates detection of amplified target nucleic acid. Nucleic acid from *Mycoplasma pneumoniae* and *Mycoplasma genitalium* were amplified by heating to 95° C., followed by 30 rounds of temperature cycling at 55° C. (30 seconds), 60° C. (60 seconds) and 95° C. (60 seconds), followed by seven minutes at 60° C. Amplification took place in 100 µl of a solution containing 50 mM potassium chloride, 10 mM Tris HCl pH 8.3, 1.5 mM magnesium chloride, 0.25 mM dATP, 0.25 mM dTTP, 0.25 mM dGTP, 0.25 mM dCTP, 2.5 U of Taq polymerase, 1 FM primer SEQ. ID. NO. 83 and 1 µM primer SEQ. ID. NO. 84. Ten microliters of the final reaction was assayed by hybridization with acridinium ester-labeled probe having the nucleotide sequence of SEQ. ID. NO. 85 and unlabeled helper probes having the nucleotide sequences of SEQ. ID. NOs. 9 and 10, or a probe directed to a nucleotide sequence perfectly complementary to *Mycoplasma genitalium* rRNA (SEQ. ID. NO. 86).

TABLE 7

ABILITY OF SPECIES SPECIFIC MYCOPLASMA HYBRIDIZATION ASSAY PROBES TO DETECT AMPLIFIED DNA

| Amount of Target Nucleic Acid | Probe SEQ. ID. NO. 85 | Probe SEQ. ID. NO. 86 |
|---|---|---|
| 1,000 copies M. pneumoniae DNA | 186,596 | 419 |
| 100 copies M. pneumoniae DNA | 262,031 | 361 |
| 10 copies M. pneumoniae DNA | 115,607 | 330 |
| 1,000 copies M. genitalium DNA | 1,586 | 482,398 |
| 100 copies M. genitalium DNA | 1,706 | 337,435 |
| 10 copies M. genitalium DNA | 2,098 | 398 |

These results show that the probe having the nucleotide sequence of SEQ. ID. NO. 85 was specific for *Mycoplasma pneumoniae* and that the probes can be used to detect DNA as well as RNA targets.

The data shown in the various examples described above confirm that the hybridization probes described herein are capable of distinguishing *Mycoplasma pneumoniae* from its known nearest phylogenetic neighbors. Furthermore, complementary oligonucleotide probes can detect the products of nucleic acid amplification procedures.

Other embodiments are within the following claims.

SEQUENCE LISTING ( 1 ) GENERAL INFORMATION:

( i i i ) NUMBER OF SEQUENCES: 92

( 2 ) INFORMATION FOR SEQ ID NO: 1:

( i ) SEQUENCE CHARACTERISTICS:
        ( A ) LENGTH: 35
        ( B ) TYPE: nucleic acid
        ( C ) STRANDEDNESS: single
        ( D ) TOPOLOGY: linear ( i i ) SEQUENCE DESCRIPTION: SEQ ID NO: 1:

CAGTCAAACT CTAGCCATTA CCTGCTAAAG TCATT    3 5

( 2 ) INFORMATION FOR SEQ ID NO: 2:

( i ) SEQUENCE CHARACTERISTICS:

(A) LENGTH: 28
(B) TYPE: nucleic acid
(C) STRANDEDNESS: single
(D) TOPOLOGY: linear (i i) SEQUENCE DESCRIPTION: SEQ ID NO: 2:

CACACTCTAG ATTAATAGTT TCCAATGC 28

(2) INFORMATION FOR SEQ ID NO: 3:

(i) SEQUENCE CHARACTERISTICS:
(A) LENGTH: 22
(B) TYPE: nucleic acid
(C) STRANDEDNESS: single
(D) TOPOLOGY: linear (i i) SEQUENCE DESCRIPTION: SEQ ID NO: 3:

CATGCGCTTC CTAATGGTTA GC 22

(2) INFORMATION FOR SEQ ID NO: 4:

(i) SEQUENCE CHARACTERISTICS:
(A) LENGTH: 25
(B) TYPE: nucleic acid
(C) STRANDEDNESS: single
(D) TOPOLOGY: linear (i i) SEQUENCE DESCRIPTION: SEQ ID NO: 4:

GCTGTTTCCA ACTACCGGAT TGCTC 25

(2) INFORMATION FOR SEQ ID NO: 5:

(i) SEQUENCE CHARACTERISTICS:
(A) LENGTH: 30
(B) TYPE: nucleic acid
(C) STRANDEDNESS: single
(D) TOPOLOGY: linear (i i) SEQUENCE DESCRIPTION: SEQ ID NO: 5:

CCTACAACCC CTATCTAATG ATAAGTTTGG 30

(2) INFORMATION FOR SEQ ID NO: 6:

(i) SEQUENCE CHARACTERISTICS:
(A) LENGTH: 26
(B) TYPE: nucleic acid
(C) STRANDEDNESS: single
(D) TOPOLOGY: linear (i i) SEQUENCE DESCRIPTION: SEQ ID NO: 6:

GCTTCTTCTA TCGTTTTCAA GTCCAC 26

(2) INFORMATION FOR SEQ ID NO: 7:

(i) SEQUENCE CHARACTERISTICS:
(A) LENGTH: 20
(B) TYPE: nucleic acid
(C) STRANDEDNESS: single
(D) TOPOLOGY: linear (i i) SEQUENCE DESCRIPTION: SEQ ID NO: 7:

CCTTTTGCGC GCTGCTTTCC 20

(2) INFORMATION FOR SEQ ID NO: 8:

(i) SEQUENCE CHARACTERISTICS:
(A) LENGTH: 28
(B) TYPE: nucleic acid (C) STRANDEDNESS: single
(D) TOPOLOGY: linear (ii) SEQUENCE DESCRIPTION: SEQ ID NO: 8:

CGTCTACCAC AAGATATAAA TCTTATCC 28

(2) INFORMATION FOR SEQ ID NO: 9:

(i) SEQUENCE CHARACTERISTICS:
(A) LENGTH: 53
(B) TYPE: nucleic acid
(C) STRANDEDNESS: single
(D) TOPOLOGY: linear (ii) SEQUENCE DESCRIPTION: SEQ ID NO: 9:

CTTCCCAAAT AAATGAACTT TACAATCTTA AAGACCTTCA TCGTTCACGC 50

GGC 53

(2) INFORMATION FOR SEQ ID NO: 10:

(i) SEQUENCE CHARACTERISTICS:
(A) LENGTH: 45
(B) TYPE: nucleic acid
(C) STRANDEDNESS: single
(D) TOPOLOGY: linear (ii) SEQUENCE DESCRIPTION: SEQ ID NO: 10:

CGCGACTGCT GGCACATAGT TAGTCGTCAC TTATTCAAAA TGGTA 45

(2) INFORMATION FOR SEQ ID NO: 11:

(i) SEQUENCE CHARACTERISTICS:
(A) LENGTH: 32
(B) TYPE: nucleic acid
(C) STRANDEDNESS: single
(D) TOPOLOGY: linear (ii) SEQUENCE DESCRIPTION: SEQ ID NO: 11:

GCAGCTGCCT TTAACACCAG ACTTTTCAAT CC 32

(2) INFORMATION FOR SEQ ID NO: 12:

(i) SEQUENCE CHARACTERISTICS:
(A) LENGTH: 37
(B) TYPE: nucleic acid
(C) STRANDEDNESS: single
(D) TOPOLOGY: linear (ii) SEQUENCE DESCRIPTION: SEQ ID NO: 12:

CTACGCATTT CACCGCTCCA CATGAAATTC CAAAACT 37

(2) INFORMATION FOR SEQ ID NO: 13:

(i) SEQUENCE CHARACTERISTICS:
(A) LENGTH: 44
(B) TYPE: nucleic acid
(C) STRANDEDNESS: single
(D) TOPOLOGY: linear (ii) SEQUENCE DESCRIPTION: SEQ ID NO: 13:

AACACGTTTT TAAATATTAC CAGCTTTCAT AGTTTGACGG GCGG 44

(2) INFORMATION FOR SEQ ID NO: 14:

(i) SEQUENCE CHARACTERISTICS:
(A) LENGTH: 31
(B) TYPE: nucleic acid (C) STRANDEDNESS: single
(D) TOPOLOGY: linear (i i) SEQUENCE DESCRIPTION: SEQ ID NO: 14:

CGACTTCACT CCAATCACCG GTGCTATCCT T                    31

(2) INFORMATION FOR SEQ ID NO: 15:

(i) SEQUENCE CHARACTERISTICS:
    (A) LENGTH: 36
    (B) TYPE: nucleic acid
    (C) STRANDEDNESS: single
    (D) TOPOLOGY: linear (i i) SEQUENCE DESCRIPTION: SEQ ID NO: 15:

CATTCGGAAA TCTCCGGATC TGAGGTTCTT ACCACC               36

(2) INFORMATION FOR SEQ ID NO: 16:

(i) SEQUENCE CHARACTERISTICS:
    (A) LENGTH: 33
    (B) TYPE: nucleic acid
    (C) STRANDEDNESS: single
    (D) TOPOLOGY: linear (i i) SEQUENCE DESCRIPTION: SEQ ID NO: 16:

CACGTATCGC TTTAATATGA CTATTTATTC ATC                  33

(2) INFORMATION FOR SEQ ID NO: 17:

(i) SEQUENCE CHARACTERISTICS:
    (A) LENGTH: 29
    (B) TYPE: nucleic acid
    (C) STRANDEDNESS: single
    (D) TOPOLOGY: linear (i i) SEQUENCE DESCRIPTION: SEQ ID NO: 17:

TGTTCCGCTT TCGCTCGCCA CTACACACG                       29

(2) INFORMATION FOR SEQ ID NO: 18:

(i) SEQUENCE CHARACTERISTICS:
    (A) LENGTH: 41
    (B) TYPE: nucleic acid
    (C) STRANDEDNESS: single
    (D) TOPOLOGY: linear (i i) SEQUENCE DESCRIPTION: SEQ ID NO: 18:

CTCGCTAGGT ATGAAAACAA TTTCAAATAC GGGGCTATCA C         41

(2) INFORMATION FOR SEQ ID NO: 19:

(i) SEQUENCE CHARACTERISTICS:
    (A) LENGTH: 42
    (B) TYPE: nucleic acid
    (C) STRANDEDNESS: single
    (D) TOPOLOGY: linear (i i) SEQUENCE DESCRIPTION: SEQ ID NO: 19:

ATAAATTCGG TAATATACTT AGCCCCGTTA CATCTTCGGC GC        42

(2) INFORMATION FOR SEQ ID NO: 20:

(i) SEQUENCE CHARACTERISTICS:
    (A) LENGTH: 34
    (B) TYPE: nucleic acid
    (C) STRANDEDNESS: single
    (D) TOPOLOGY: linear (ii) SEQUENCE DESCRIPTION: SEQ ID NO: 20:

GCTCACGCTT TGACTTCAAC TCCAATACAA CGCT        34

(2) INFORMATION FOR SEQ ID NO: 21:

(i) SEQUENCE CHARACTERISTICS:
      (A) LENGTH: 35
      (B) TYPE: nucleic acid
      (C) STRANDEDNESS: single
      (D) TOPOLOGY: linear (ii) SEQUENCE DESCRIPTION: SEQ ID NO: 21:

AATGACTTTA GCAGGTAATG CTAGAGTTT GACTG        35

(2) INFORMATION FOR SEQ ID NO: 22:

(i) SEQUENCE CHARACTERISTICS:
      (A) LENGTH: 35
      (B) TYPE: nucleic acid
      (C) STRANDEDNESS: single
      (D) TOPOLOGY: linear (ii) SEQUENCE DESCRIPTION: SEQ ID NO: 22:

CAGUCAAACU CUAGCCAUUA CCUGCUAAAG UCAUU        35

(2) INFORMATION FOR SEQ ID NO: 23:

(i) SEQUENCE CHARACTERISTICS:
      (A) LENGTH: 35
      (B) TYPE: nucleic acid
      (C) STRANDEDNESS: single
      (D) TOPOLOGY: linear (ii) SEQUENCE DESCRIPTION: SEQ ID NO: 23:

AAUGACUUUA GCAGGUAAUG GCUAGAGUUU GACUG        35

(2) INFORMATION FOR SEQ ID NO: 24:

(i) SEQUENCE CHARACTERISTICS:
      (A) LENGTH: 28
      (B) TYPE: nucleic acid
      (C) STRANDEDNESS: single
      (D) TOPOLOGY: linear (ii) SEQUENCE DESCRIPTION: SEQ ID NO: 24:

GCATTGGAAA CTATTAATCT AGAGTGTG        28

(2) INFORMATION FOR SEQ ID NO: 25:

(i) SEQUENCE CHARACTERISTICS:
      (A) LENGTH: 28
      (B) TYPE: nucleic acid
      (C) STRANDEDNESS: single
      (D) TOPOLOGY: linear (ii) SEQUENCE DESCRIPTION: SEQ ID NO: 25:

CACACUCUAG AUUAAUAGUU UCCAAUGC        28

(2) INFORMATION FOR SEQ ID NO: 26:

(i) SEQUENCE CHARACTERISTICS:
      (A) LENGTH: 28
      (B) TYPE: nucleic acid
      (C) STRANDEDNESS: single
      (D) TOPOLOGY: linear (ii) SEQUENCE DESCRIPTION: SEQ ID NO: 26:

GCAUUGGAAA CUAUUAAUCU AGAGUGUG  28

( 2 ) INFORMATION FOR SEQ ID NO: 27:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 27:

GCTAACCATT AGGAAGCGCA TG  22

( 2 ) INFORMATION FOR SEQ ID NO: 28:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 28:

CAUGCGCUUC CUAAUGGUUA GC  22

( 2 ) INFORMATION FOR SEQ ID NO: 29:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 29:

GCUAACCAUU AGGAAGCGCA UG  22

( 2 ) INFORMATION FOR SEQ ID NO: 30:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) SEQUENCE DESCRIPTION: SEQ ID NO: 30:

GAGCAATCCG GTAGTTGGAA ACAGC  25

( 2 ) INFORMATION FOR SEQ ID NO: 31:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) SEQUENCE DESCRIPTION: SEQ ID NO: 31:

GCUGUUUCCA ACUACCGGAU UGCUC  25

( 2 ) INFORMATION FOR SEQ ID NO: 32:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) SEQUENCE DESCRIPTION: SEQ ID NO: 32:

GAGCAAUCCG GUAGUUGGAA ACAGC  25

( 2 ) INFORMATION FOR SEQ ID NO: 33:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( i i ) SEQUENCE DESCRIPTION: SEQ ID NO: 33:

CCAAACTTAT CATTAGATAG GGGTTGTAGG            30

( 2 ) INFORMATION FOR SEQ ID NO: 34:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( i i ) SEQUENCE DESCRIPTION: SEQ ID NO: 34:

CCUACAACCC CUAUCUAAUG AUAAGUUUGG           30

( 2 ) INFORMATION FOR SEQ ID NO: 35:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( i i ) SEQUENCE DESCRIPTION: SEQ ID NO: 35:

CCAAACUUAU CAUUAGAUAG GGGUUGUAGG           30

( 2 ) INFORMATION FOR SEQ ID NO: 36:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear ( i i ) SEQUENCE DESCRIPTION: SEQ ID NO: 36:

GTGGACTTGA AAACGATAGA AGAAGC                26

( 2 ) INFORMATION FOR SEQ ID NO: 37:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear ( i i ) SEQUENCE DESCRIPTION: SEQ ID NO: 37:

GCUUCUUCUA UCGUUUUCAA GUCCAC                26

( 2 ) INFORMATION FOR SEQ ID NO: 38:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear ( i i ) SEQUENCE DESCRIPTION: SEQ ID NO: 38:

GUGGACUUGA AAACGAUAGA AGAAGC                26

( 2 ) INFORMATION FOR SEQ ID NO: 39:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( i i ) SEQUENCE DESCRIPTION: SEQ ID NO: 39:

GGAAAGCAGC GCGCAAAAGG             20

( 2 ) INFORMATION FOR SEQ ID NO: 40:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( i i ) SEQUENCE DESCRIPTION: SEQ ID NO: 40:

CCUUUUGCGC GCUGCUUUCC             20

( 2 ) INFORMATION FOR SEQ ID NO: 41:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( i i ) SEQUENCE DESCRIPTION: SEQ ID NO: 41:

GGAAAGCAGC GCGCAAAAGG             20

( 2 ) INFORMATION FOR SEQ ID NO: 42:

( i ) SEQUENCE CHARACTERISTICS:
    ( A ) LENGTH: 28
    ( B ) TYPE: nucleic acid
    ( C ) STRANDEDNESS: single
    ( D ) TOPOLOGY: linear ( i i ) SEQUENCE DESCRIPTION: SEQ ID NO: 42:

GGATAAGATT TATATCTTGT GGTAGACG          28

( 2 ) INFORMATION FOR SEQ ID NO: 43:

( i ) SEQUENCE CHARACTERISTICS:
    ( A ) LENGTH: 28
    ( B ) TYPE: nucleic acid
    ( C ) STRANDEDNESS: single
    ( D ) TOPOLOGY: linear ( i i ) SEQUENCE DESCRIPTION: SEQ ID NO: 43:

CGUCUACCAC AAGAUAUAAA UCUUAUCC          28

( 2 ) INFORMATION FOR SEQ ID NO: 44:

( i ) SEQUENCE CHARACTERISTICS:
    ( A ) LENGTH: 28
    ( B ) TYPE: nucleic acid
    ( C ) STRANDEDNESS: single
    ( D ) TOPOLOGY: linear ( i i ) SEQUENCE DESCRIPTION: SEQ ID NO: 44:

GGAUAAGAUU UAUAUCUUGU GGUAGACG          28

( 2 ) INFORMATION FOR SEQ ID NO: 45:

( i ) SEQUENCE CHARACTERISTICS:
( A ) LENGTH: 53
( B ) TYPE: nucleic acid
( C ) STRANDEDNESS: single
( D ) TOPOLOGY: linear ( i i ) SEQUENCE DESCRIPTION: SEQ ID NO: 45:

GCCGCGTGAA CGATGAAGGT CTTTAAGATT GTAAAGTTCA TTTATTTGGG    50

AAG    53

( 2 ) INFORMATION FOR SEQ ID NO: 46:

( i ) SEQUENCE CHARACTERISTICS:
( A ) LENGTH: 53
( B ) TYPE: nucleic acid
( C ) STRANDEDNESS: single
( D ) TOPOLOGY: linear ( i i ) SEQUENCE DESCRIPTION: SEQ ID NO: 46:

CUUCCCAAAU AAAUGAACUU UACAAUCUUA AAGACCUUCA UCGUUCACGC    50

GGC    53

( 2 ) INFORMATION FOR SEQ ID NO: 47:

( i ) SEQUENCE CHARACTERISTICS:
( A ) LENGTH: 53
( B ) TYPE: nucleic acid
( C ) STRANDEDNESS: single
( D ) TOPOLOGY: linear ( i i ) SEQUENCE DESCRIPTION: SEQ ID NO: 47:

GCCGCGUGAA CGAUGAAGGU CUUUAAGAUU GUAAAGUUCA UUUAUUUGGG    50

AAG    53

( 2 ) INFORMATION FOR SEQ ID NO: 48:

( i ) SEQUENCE CHARACTERISTICS:
( A ) LENGTH: 45
( B ) TYPE: nucleic acid
( C ) STRANDEDNESS: single
( D ) TOPOLOGY: linear ( i i ) SEQUENCE DESCRIPTION: SEQ ID NO: 48:

TACCATTTTG AATAAGTGAC GACTAACTAT GTGCCAGCAG TCGCG    45

( 2 ) INFORMATION FOR SEQ ID NO: 49:

( i ) SEQUENCE CHARACTERISTICS:
( A ) LENGTH: 45
( B ) TYPE: nucleic acid
( C ) STRANDEDNESS: single
( D ) TOPOLOGY: linear ( i i ) SEQUENCE DESCRIPTION: SEQ ID NO: 49:

CGCGACUGCU GGCACAUAGU UAGUCGUCAC UUAUUCAAAA UGGUA    45

( 2 ) INFORMATION FOR SEQ ID NO: 50:

( i ) SEQUENCE CHARACTERISTICS:
( A ) LENGTH: 45
( B ) TYPE: nucleic acid
( C ) STRANDEDNESS: single
( D ) TOPOLOGY: linear ( i i ) SEQUENCE DESCRIPTION: SEQ ID NO: 50:

UACCAUUUUG AAUAAGUGAC GACUAACUAU GUGCCAGCAG UCGCG    45

( 2 ) INFORMATION FOR SEQ ID NO: 51:

( i ) SEQUENCE CHARACTERISTICS:
    ( A ) LENGTH: 32
    ( B ) TYPE: nucleic acid
    ( C ) STRANDEDNESS: single
    ( D ) TOPOLOGY: linear ( i i ) SEQUENCE DESCRIPTION: SEQ ID NO: 51:

GGATTGAAAA GTCTGGTGTT AAAGGCAGCT GC        32

( 2 ) INFORMATION FOR SEQ ID NO: 52:

( i ) SEQUENCE CHARACTERISTICS:
    ( A ) LENGTH: 32
    ( B ) TYPE: nucleic acid
    ( C ) STRANDEDNESS: single
    ( D ) TOPOLOGY: linear ( i i ) SEQUENCE DESCRIPTION: SEQ ID NO: 52:

GCAGCUGCCU UUAACACCAG ACUUUCAAU CC        32

( 2 ) INFORMATION FOR SEQ ID NO: 53:

( i ) SEQUENCE CHARACTERISTICS:
    ( A ) LENGTH: 32
    ( B ) TYPE: nucleic acid
    ( C ) STRANDEDNESS: single
    ( D ) TOPOLOGY: linear ( i i ) SEQUENCE DESCRIPTION: SEQ ID NO: 53:

GGAUUGAAAA GUCUGGUGUU AAAGGCAGCU GC        32

( 2 ) INFORMATION FOR SEQ ID NO: 54:

( i ) SEQUENCE CHARACTERISTICS:
    ( A ) LENGTH: 37
    ( B ) TYPE: nucleic acid
    ( C ) STRANDEDNESS: single
    ( D ) TOPOLOGY: linear ( i i ) SEQUENCE DESCRIPTION: SEQ ID NO: 54:

AGTTTTGGAA TTTCATGTGG AGCGGTGAAA TGCGTAG        37

( 2 ) INFORMATION FOR SEQ ID NO: 55:

( i ) SEQUENCE CHARACTERISTICS:
    ( A ) LENGTH: 37
    ( B ) TYPE: nucleic acid
    ( C ) STRANDEDNESS: single
    ( D ) TOPOLOGY: linear ( i i ) SEQUENCE DESCRIPTION: SEQ ID NO: 55:

CUACGCAUUU CACCGCUCCA CAUGAAAUUC CAAAACU        37

( 2 ) INFORMATION FOR SEQ ID NO: 56:

( i ) SEQUENCE CHARACTERISTICS:
    ( A ) LENGTH: 37
    ( B ) TYPE: nucleic acid
    ( C ) STRANDEDNESS: single
    ( D ) TOPOLOGY: linear ( i i ) SEQUENCE DESCRIPTION: SEQ ID NO: 56:

AGUUUUGGAA UUUCAUGUGG AGCGGUGAAA UGCGUAG        37

( 2 ) INFORMATION FOR SEQ ID NO: 57:

( i ) SEQUENCE CHARACTERISTICS:
        ( A ) LENGTH: 44
        ( B ) TYPE: nucleic acid
        ( C ) STRANDEDNESS: single
        ( D ) TOPOLOGY: linear ( i i ) SEQUENCE DESCRIPTION: SEQ ID NO: 57:

CCGCCCGTCA AACTATGAAA GCTGGTAATA TTTAAAAACG TGTT        44

( 2 ) INFORMATION FOR SEQ ID NO: 58:

( i ) SEQUENCE CHARACTERISTICS:
        ( A ) LENGTH: 41
        ( B ) TYPE: nucleic acid
        ( C ) STRANDEDNESS: single
        ( D ) TOPOLOGY: linear ( i i ) SEQUENCE DESCRIPTION: SEQ ID NO: 58:

AACACGUUUU UAAAUAUUAC CAGCUUUCAU AGUUUGACGG G        41

( 2 ) INFORMATION FOR SEQ ID NO: 59:

( i ) SEQUENCE CHARACTERISTICS:
        ( A ) LENGTH: 44
        ( B ) TYPE: nucleic acid
        ( C ) STRANDEDNESS: single
        ( D ) TOPOLOGY: linear ( i i ) SEQUENCE DESCRIPTION: SEQ ID NO: 59:

CCGCCCGUCA AACUAUGAAA GCUGGUAAUA UUUAAAAACG UGUU        44

( 2 ) INFORMATION FOR SEQ ID NO: 60:

( i ) SEQUENCE CHARACTERISTICS:
        ( A ) LENGTH: 31
        ( B ) TYPE: nucleic acid
        ( C ) STRANDEDNESS: single
        ( D ) TOPOLOGY: linear ( i i ) SEQUENCE DESCRIPTION: SEQ ID NO: 60:

AAGGATAGCA CCGGTGATTG GAGTGAAGTC G        31

( 2 ) INFORMATION FOR SEQ ID NO: 61:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( i i ) SEQUENCE DESCRIPTION: SEQ ID NO: 61:

CGCCACUGGU GUUCCUUCAU AUAUCUACGC        30

( 2 ) INFORMATION FOR SEQ ID NO: 62:

( i ) SEQUENCE CHARACTERISTICS:
        ( A ) LENGTH: 31
        ( B ) TYPE: nucleic acid
        ( C ) STRANDEDNESS: single
        ( D ) TOPOLOGY: linear ( i i ) SEQUENCE DESCRIPTION: SEQ ID NO: 62:

CGACUUCACU CCAAUCACCG GUGCUAUCCU U        31

( 2 ) INFORMATION FOR SEQ ID NO: 63:

( i ) SEQUENCE CHARACTERISTICS:
    ( A ) LENGTH: 31
    ( B ) TYPE: nucleic acid
    ( C ) STRANDEDNESS: single
    ( D ) TOPOLOGY: linear ( i i ) SEQUENCE DESCRIPTION: SEQ ID NO: 63:

AAGGAUAGCA CCGGUGAUUG GAGUGAAGUC G          31

( 2 ) INFORMATION FOR SEQ ID NO: 64:

( i ) SEQUENCE CHARACTERISTICS:
    ( A ) LENGTH: 36
    ( B ) TYPE: nucleic acid
    ( C ) STRANDEDNESS: single
    ( D ) TOPOLOGY: linear ( i i ) SEQUENCE DESCRIPTION: SEQ ID NO: 64:

GGTGGTAAGA ACCTCAGATC CGGAGATTTC CGAATG      36

( 2 ) INFORMATION FOR SEQ ID NO: 65:

( i ) SEQUENCE CHARACTERISTICS:
    ( A ) LENGTH: 36
    ( B ) TYPE: nucleic acid
    ( C ) STRANDEDNESS: single
    ( D ) TOPOLOGY: linear ( i i ) SEQUENCE DESCRIPTION: SEQ ID NO: 65:

CAUUCGGAAA UCUCCGGAUC UGAGGUUCUU ACCACC      36

( 2 ) INFORMATION FOR SEQ ID NO: 66:

( i ) SEQUENCE CHARACTERISTICS:
    ( A ) LENGTH: 36
    ( B ) TYPE: nucleic acid
    ( C ) STRANDEDNESS: single
    ( D ) TOPOLOGY: linear ( i i ) SEQUENCE DESCRIPTION: SEQ ID NO: 66:

GGUGGUAAGA ACCUCAGAUC CGGAGAUUUC CGAAUG      36

( 2 ) INFORMATION FOR SEQ ID NO: 67:

( i ) SEQUENCE CHARACTERISTICS:
    ( A ) LENGTH: 33
    ( B ) TYPE: nucleic acid
    ( C ) STRANDEDNESS: single
    ( D ) TOPOLOGY: linear ( i i ) SEQUENCE DESCRIPTION: SEQ ID NO: 67:

GATGAATAAA TAGTCATATT AAAGCGATAC GTG        33

( 2 ) INFORMATION FOR SEQ ID NO: 68:

( i ) SEQUENCE CHARACTERISTICS:
    ( A ) LENGTH: 33
    ( B ) TYPE: nucleic acid
    ( C ) STRANDEDNESS: single
    ( D ) TOPOLOGY: linear ( i i ) SEQUENCE DESCRIPTION: SEQ ID NO: 68:

CACGUAUCGC UUUAAUAUGA CUAUUUAUUC AUC        33

( 2 ) INFORMATION FOR SEQ ID NO: 69:

( i ) SEQUENCE CHARACTERISTICS:
    ( A ) LENGTH: 33

```
              ( B ) TYPE: nucleic acid
              ( C ) STRANDEDNESS: single
              ( D ) TOPOLOGY: linear ( i i ) SEQUENCE DESCRIPTION: SEQ ID NO: 69:

GAUGAAUAAA UAGUCAUAUU AAAGCGAUAC GUG                           33

( 2 ) INFORMATION FOR SEQ ID NO: 70:

( i ) SEQUENCE CHARACTERISTICS:
              ( A ) LENGTH: 28
              ( B ) TYPE: nucleic acid
              ( C ) STRANDEDNESS: single
              ( D ) TOPOLOGY: linear ( i i ) SEQUENCE DESCRIPTION: SEQ ID NO: 70:

CGTGTGTAGT GGCGAGCGAA AGCGGAAC                                 28

( 2 ) INFORMATION FOR SEQ ID NO: 71:

( i ) SEQUENCE CHARACTERISTICS:
              ( A ) LENGTH: 29
              ( B ) TYPE: nucleic acid
              ( C ) STRANDEDNESS: single
              ( D ) TOPOLOGY: linear ( i i ) SEQUENCE DESCRIPTION: SEQ ID NO: 71:

UGUUCCGCUU UCGCUCGCCA CUACACACG                                29

( 2 ) INFORMATION FOR SEQ ID NO: 72:

( i ) SEQUENCE CHARACTERISTICS:
              ( A ) LENGTH: 29
              ( B ) TYPE: nucleic acid
              ( C ) STRANDEDNESS: single
              ( D ) TOPOLOGY: linear ( i i ) SEQUENCE DESCRIPTION: SEQ ID NO: 72:

CGUGUGUAGU GGCGAGCGAA AGCGGAACA                                29

( 2 ) INFORMATION FOR SEQ ID NO: 73:

( i ) SEQUENCE CHARACTERISTICS:
              ( A ) LENGTH: 41
              ( B ) TYPE: nucleic acid
              ( C ) STRANDEDNESS: single
              ( D ) TOPOLOGY: linear ( i i ) SEQUENCE DESCRIPTION: SEQ ID NO: 73:

GTGATAGCCC CGTATTTGAA ATTGTTTTCA TACCTAGCGA G                  41

( 2 ) INFORMATION FOR SEQ ID NO: 74:

( i ) SEQUENCE CHARACTERISTICS:
              ( A ) LENGTH: 41
              ( B ) TYPE: nucleic acid
              ( C ) STRANDEDNESS: single
              ( D ) TOPOLOGY: linear ( i i ) SEQUENCE DESCRIPTION: SEQ ID NO: 74:

CUCGCUAGGU AUGAAAACAA UUUCAAAUAC GGGGCUAUCA C                  41

( 2 ) INFORMATION FOR SEQ ID NO: 75:

( i ) SEQUENCE CHARACTERISTICS:
              ( A ) LENGTH: 41
              ( B ) TYPE: nucleic acid
              ( C ) STRANDEDNESS: single
```

( D ) TOPOLOGY: linear ( i i ) SEQUENCE DESCRIPTION: SEQ ID NO: 75:

GUGAUAGCCC CGUAUUUGAA AUUGUUUUCA UACCUAGCGA G      41

( 2 ) INFORMATION FOR SEQ ID NO: 76:

( i ) SEQUENCE CHARACTERISTICS:
        ( A ) LENGTH: 42
        ( B ) TYPE: nucleic acid
        ( C ) STRANDEDNESS: single
        ( D ) TOPOLOGY: linear ( i i ) SEQUENCE DESCRIPTION: SEQ ID NO: 76:

GCGCCGAAGA TGTAACGGGG CTAAGTATAT TACCGAATTT AT      42

( 2 ) INFORMATION FOR SEQ ID NO: 77:

( i ) SEQUENCE CHARACTERISTICS:
        ( A ) LENGTH: 42
        ( B ) TYPE: nucleic acid
        ( C ) STRANDEDNESS: single
        ( D ) TOPOLOGY: linear ( i i ) SEQUENCE DESCRIPTION: SEQ ID NO: 77:

AUAAAUUCGG UAAUAUACUU AGCCCGUUA CAUCUUCGGC GC      42

( 2 ) INFORMATION FOR SEQ ID NO: 78:

( i ) SEQUENCE CHARACTERISTICS:
        ( A ) LENGTH: 42
        ( B ) TYPE: nucleic acid
        ( C ) STRANDEDNESS: single
        ( D ) TOPOLOGY: linear ( i i ) SEQUENCE DESCRIPTION: SEQ ID NO: 78:

GCGCCGAAGA UGUAACGGGG CUAAGUAUAU UACCGAAUUU AU      42

( 2 ) INFORMATION FOR SEQ ID NO: 79:

( i ) SEQUENCE CHARACTERISTICS:
        ( A ) LENGTH: 34
        ( B ) TYPE: nucleic acid
        ( C ) STRANDEDNESS: single
        ( D ) TOPOLOGY: linear ( i i ) SEQUENCE DESCRIPTION: SEQ ID NO: 79:

AGCGTTGTAT TGGAGTTGAA GTCAAAGCGT GAGC      34

( 2 ) INFORMATION FOR SEQ ID NO: 80:

( i ) SEQUENCE CHARACTERISTICS:
        ( A ) LENGTH: 34
        ( B ) TYPE: nucleic acid
        ( C ) STRANDEDNESS: single
        ( D ) TOPOLOGY: linear ( i i ) SEQUENCE DESCRIPTION: SEQ ID NO: 80:

GCUCACGCUU UGACUUCAAC UCCAAUACAA CGCU      34

( 2 ) INFORMATION FOR SEQ ID NO: 81:

( i ) SEQUENCE CHARACTERISTICS:
        ( A ) LENGTH: 34
        ( B ) TYPE: nucleic acid
        ( C ) STRANDEDNESS: single
        ( D ) TOPOLOGY: linear ( i i ) SEQUENCE DESCRIPTION: SEQ ID NO: 81:

AGCGUUGUAU UGGAGUUGAA GUCAAAGCGU GAGC    34

( 2 ) INFORMATION FOR SEQ ID NO: 82:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( i i ) SEQUENCE DESCRIPTION: SEQ ID NO: 82:

CGCCACTGGT GTTCCTTCAT ATATCTACGC    30

( 2 ) INFORMATION FOR SEQ ID NO: 83:

( i ) SEQUENCE CHARACTERISTICS:
        ( A ) LENGTH: 31
        ( B ) TYPE: nucleic acid
        ( C ) STRANDEDNESS: single
        ( D ) TOPOLOGY: linear ( i i ) SEQUENCE DESCRIPTION: SEQ ID NO: 83:

ATCAAAGTTG AAAGGACCTG CAAGGGTTCG T    31

( 2 ) INFORMATION FOR SEQ ID NO: 84:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) SEQUENCE DESCRIPTION: SEQ ID NO: 84:

CTGCTGGCAC ATAGTTAGTC GTC    23

( 2 ) INFORMATION FOR SEQ ID NO: 85:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) SEQUENCE DESCRIPTION: SEQ ID NO: 85:

CTCTAGCCAT TACCTGCTAA AGTC    24

( 2 ) INFORMATION FOR SEQ ID NO: 86:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) SEQUENCE DESCRIPTION: SEQ ID NO: 86:

GAATGACTCT AGCAGGCAAT GGC    23

( 2 ) INFORMATION FOR SEQ ID NO: 87:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) SEQUENCE DESCRIPTION: SEQ ID NO: 87:

| | |
|---|---|
| GACTTTAGCA GGTAATGGCT AGAG | 24 |

(2) INFORMATION FOR SEQ ID NO: 88:

(i) SEQUENCE CHARACTERISTICS:
        (A) LENGTH: 24
        (B) TYPE: nucleic acid
        (C) STRANDEDNESS: single
        (D) TOPOLOGY: linear (ii) SEQUENCE DESCRIPTION: SEQ ID NO: 88:

| | |
|---|---|
| CUCUAGCCAU UACCUGCUAA AGUC | 24 |

(2) INFORMATION FOR SEQ ID NO: 89:

(i) SEQUENCE CHARACTERISTICS:
        (A) LENGTH: 24
        (B) TYPE: nucleic acid
        (C) STRANDEDNESS: single
        (D) TOPOLOGY: linear (ii) SEQUENCE DESCRIPTION: SEQ ID NO: 89:

| | |
|---|---|
| GACUUUAGCA GGUAAUGGCU AGAG | 24 |

(2) INFORMATION FOR SEQ ID NO: 90:

(i) SEQUENCE CHARACTERISTICS:
        (A) LENGTH: 31
        (B) TYPE: nucleic acid
        (C) STRANDEDNESS: single
        (D) TOPOLOGY: linear (ii) SEQUENCE DESCRIPTION: SEQ ID NO: 90:

| | |
|---|---|
| AUCAAAGUUG AAAGGACCUG CAAGGGUUCG U | 31 |

(2) INFORMATION FOR SEQ ID NO: 91:

(i) SEQUENCE CHARACTERISTICS:
        (A) LENGTH: 23
        (B) TYPE: nucleic acid
        (C) STRANDEDNESS: single
        (D) TOPOLOGY: linear (ii) SEQUENCE DESCRIPTION: SEQ ID NO: 91:

| | |
|---|---|
| CUGCUGGCAC AUAGUUAGUC GUC | 23 |

(2) INFORMATION FOR SEQ ID NO: 92:

(i) SEQUENCE CHARACTERISTICS:
        (A) LENGTH: 27
        (B) TYPE: nucleic acid
        (C) STRANDEDNESS: single
        (D) TOPOLOGY: linear (ii) SEQUENCE DESCRIPTION: SEQ ID NO: 92:

| | |
|---|---|
| AATTAATAC GACTCACTAT AGGGAGA | 27 |

What is claimed is:

1. A method for detecting the presence of *Mycoplasma pneumoniae* and distinguishing said *Mycoplasma pneumoniae* from *Mycoplasma genitalium, Mycoplasma orals, Mycoplasma faucium, Mycoplasma buccale,* or *Mycoplasma salivarium*, comprising the steps of:

a) contacting a test sample under stringent hybridization assay conditions with a nucleic acid hybridization assay probe which forms a hybrid stable for detection under said conditions with *Mycoplasma pneumonias* nucleic acid, wherein said probe comprises a nucleotide sequence which is at least 90% complementary to at least 10 contiguous nucleotides present in a target sequence selected from the group consisting of:

| SEQ ID NO: 2 | CACACTCTAG | ATTAATAGTT | TCCAATGC, |
|---|---|---|---|
| SEQ ID NO: 3 | CATGCGCTTC | CTAATGGTTA | GC, |
| SEQ ID NO: 4 | GCTGTTTCCA | ACTACCGGAT | TGCTC, |
| SEQ ID NO: 7 | CCTTTTGCGC | GCTGCTTTCC, | |
| SEQ ID NO: 8 | CGTCTACCAC | AAGATATAAA | TCTTATCC, |
| SEQ ID NO: 26 | GCAUUGGAAA | CUAUUAAUCU | AGAGUGUG, |
| SEQ ID NO: 29 | GCUAACCAUU | AGGAAGCGCA | UG, |
| SEQ ID NO: 32 | GAGCAAUCCG | GUAGUUGGAA | ACAGC, |
| SEQ ID NO: 41 | GGAAAGCAGC | GCGCAAAAGG, | and |
| SEQ ID NO: 44 | GGAUAAGAUU | UAUAUCUUGU | GGUAGACG, | wherein, said probe preferentially hybridizes to said *Mycoplasma pneumonias* nucleic acid over nucleic acids present in *Mycoplasma genitalium*, *Mycoplasma orale*, *Mycoplasma faucium*, *Mycoplasma buccale*, or *Mycoplasma salivarium* under said conditions; and b) measuring the presence or amount of said probe hybridized to said *Mycoplasma pneumoniae* nucleic acid in said test sample as an indication of the presence or amount of said *Mycoplasma pneumoniae*.

2. The method of claim 1, wherein said target sequence is selected from the group consisting of:

| SEQ ID NO: 2: | CACACTATAG ATTAATAGTT TCCAATGC, and |
|---|---|
| SEQ ID NO: 26: | GCAUUGGAAA CUAUUAAUCU AGAGUGUG. |

3. The method of claim 1, wherein said target sequence is selected from the group consisting of:

| SEQ ID NO: 3: | CATGCGCTTC CTAATGGTTA GC, and |
|---|---|
| SEQ ID NO: 29: | GCUAACCAUU AGGAAGCGCA UG. |

4. The method of claim 1, wherein said-target sequence is selected from the group consisting of:

| SEQ ID NO: 4: | GCTGTTTCCA ACTACCGGAT TGCTC, and |
|---|---|
| SEQ ID NO: 32: | GAGCAAUCCG GUAGUUGGAA ACAGC. |

5. The method of claim 1, wherein said target sequence is selected from the group consisting of:

| SEQ ID NO: 7: | CCTTTTGCG GCTGCTTTCC, and |
|---|---|
| SEQ ID NO: 41: | GGAAAGCAGC GCGCAAAAGG. |

6. The method of claim 1, wherein said target sequence is selected from the group consisting of:

| SEQ ID NO: 8: | CGTCTACCAC AAGATATAAA TCTTATCC, and |
|---|---|
| SEQ ID NO: 44: | GGAUAAGAUU UAUAUCUUGU GGUAGACG. |

7. The method of claim 2, wherein said probe comprises a nucleotide sequence which is 100% complementary to said at least 10 contiguous nucleotides.

8. The method of claim 3, wherein said probe comprises a nucleotide sequence which is 100% complementary to said at least 10 contiguous nucleotides.

9. The method of claim 4, wherein said probe comprises a nucleotide sequence which is 100% complementary to said at least 10 contiguous nucleotides.

10. The method of claim 5, wherein said probe comprises a nucleotide sequence which is 100% complementary to said at least 10 contiguous nucleotides.

11. The method of claim 6, wherein said probe comprises a nucleotide sequence which is 100% complementary to said at least 10 contiguous nucleotides.

12. A method for detecting a presence of *Mycoplasma pneumoniae* and distinguishing said *Mycoplasma pneumoniae* from other Mycoplasma comprising the steps of:

a) contacting a test sample under stringent hybridization assay conditions with a nucleic acid hybridization assay probe able to preferentially hybridize to a *Mycoplasma pneumoniae* target nucleic acid sequence region over nucleic acid sequence regions present in *Mycoplasma genitalium*, under said conditions, said hybridization assay probe comprising a nucleic acid sequence having no more than a 20% nucleotide base difference, excluding RNA or DNA equivalent nucleotides, than a nucleotide sequence selected from the group consisting of:

| SEQ ID NO: 2: | CACACTCTAG ATTAATAGTT TCCAATGC, |
|---|---|
| SEQ ID NO: 3: | CATGCGCTTC CTAATGGTTA GC, |
| SEQ ID NO: 4: | GCTGTTTCCA ACTACCGGAT TGCTC, |
| SEQ ID NO: 7: | CCTTTTGCGC GCTGCTTTCC, |
| SEQ ID NO: 8: | CGTCTACCAC AAGATATAAA TCTTATCC, |
| SEQ ID NO: 24: | GCATTGGAAA CTATTAATCT AGAGTGTG, |
| SEQ ID NO: 27: | GCTAACCATT AGGAAGCGCA TG, |
| SEQ ID NO: 30: | GAGCAATCCG GTAGTTGGAA ACAGC, |
| SEQ ID NO: 39: | GGAAAGCAGC GCGCAAAAGG, and |
| SEQ ID NO: 42: | GGATAAGATT TATATCTTGT GGTAGACG, and | b) measuring the presence or amount of said probe hybridized to said *Mycoplasma pneumonias* nucleic acid in said test sample as an indication of the presence or amount of said *Mycoplasma pneumoniae*.

13. The method of claim 12, further comprising the use of at least one helper probe.

14. The method of claim 12, wherein said nucleotide sequence is selected from the group consisting of:

| SEQ ID NO: 2: | CACACTCTAG ATTAATAGTT TCCAATGC, and |
|---|---|
| SEQ ID NO: 24: | GCATTGGAAA CTATTAATCT AGAGTGTG. |

15. The method of claim 12, wherein said nucleotide sequence is selected from the group consisting of:

| SEQ ID NO: 3: | CATGCGCTTC CTAATGGTTA GC, and |
|---|---|
| SEQ ID NO: 27: | GCTAACCATT AGGAAGCGCA TG. |

16. The method of claim 12, wherein said nucleotide sequence is selected from the group consisting of:

| SEQ ID NO: 4: | GCTGTTTCCA ACTACCGGAT TGCTC, and |
|---|---|
| SEQ ID NO: 30: | GAGCAATCCG GTAGTTGGAA ACAGC. |

17. The method of claim 17, wherein said nucleotide sequence is selected from the group consisting of:

| SEQ ID NO: 7: | CCTTTTGCGC GCTGCTTTCC, and |
| --- | --- |
| SEQ ID NO: 39: | GGAAAGCAGC GCGCAAAAGG. |

18. The method of claim 12, wherein said nucleotide sequence is selected from the group consisting of:

| SEQ ID NO: 8: | CGTCTACCAC AAGATATAAA TCTTATCC, and |
| --- | --- |
| SEQ ID NO: 42: | GGATAAGATT TATATCTTGT GGTAGACG. |

19. A method for detecting *Mycoplasma pneumoniae* nucleic acid comprising the steps of:

a) amplifying a *Mycoplasma pneumoniae* nucleic acid template using one or more amplification oligonucleotides, said amplification oligonucleotides being up to four nucleotides longer, or having up to two deleted nucleotides, and having no more than a 20% nucleotide base difference excluding RNA or DNA equivalent nucleotides, than an amplification sequence selected from the group consisting of:

| SEQ ID NO: 51: | GGATTGAAAA GTCTGGTGTT AAAGGCAGCT GC, |
| --- | --- |
| SEQ ID NO: 82: | CGCCACTGGT GTTCCTTCAT ATATCTACGC, |
| SEQ ID NO: 83: | ATCAAAGTTG AAAGGACCTG CAAGGGTTCG T, and |
| SEQ ID NO: 84: | CTGCTGGCAC ATAGTTAGTC GTC; and | b) detecting amplified *Mycoplasma pneumoniae* nucleic acid produced in said step a) using an oligonucleotide hybridization assay probe able to preferentially hybridize to said *Mycoplasma pneumoniae* nucleic acid over *Mycoplasma genitalium* nucleic acid under stringent hybridization conditions, wherein said hybridization assay probe comprises a nucleic acid sequence having no more than a 20% nucleotide base difference, excluding RNA or DNA equivalent nucleotides, than a detection sequence selected from the group consisting of:

| SEQ ID NO: 2: | CACACTCTAG ATTAATAGTT TCCAATGC, |
| --- | --- |
| SEQ ID NO: 24: | GCATTGGAAA CTATTAATCT AGAGTGTG, |

| SEQ ID NO: 85: | CTCTAGCCAT TACCTGCTAA AGTC, and |
| --- | --- |
| SEQ ID NO: 87: | GACTTTAGCA GGTAATGGCT AGAG. |

20. The method of claim 19, wherein said amplification oligonucleotide further comprises a nucleic acid sequence recognized by an RNA polymerase or which enhances initiation or elongation by an RNA polymerase.

21. The method of claim 19, wherein said amplification sequence is selected from the group consisting of:

| SEQ ID NO: 51: | GGATTGAAAA GTCTGGTGTT AAAGGCAGCT GC, and |
| --- | --- |
| SEQ ID NO: 82: | CGCCACTGGT GTTCCTTCAT ATATCTACGC; | and said detection sequence is

| SEQ ID NO: 24: | GCATTGGAAA CTATTAATCT AGAGTGTG. |
| --- | --- |

22. The method of claim 19, wherein said amplification sequence is selected from the group consisting of:

| SEQ ID NO: 83: | ATCAAAGTTG AAAGGACCTG CAASGGGTTCG T, |
| --- | --- |
| SEQ ID NO: 84 | CTGCTGGCAC ATAGTTAGTC GTC; | and said detection sequence is

| SEQ ID No: 85 | CTCTAGCCAT TACCTGCTAA AGTC. |
| --- | --- |

23. A method for amplifying *Mycoplasma pneumoniae* or *Mycoplasma genitalium* nucleic acid in a test sample comprising the steps of:

a) forming a hybrid comprising an amplification oligonucleotide and either a *Mycoplasma pneumonias* or a *Mycoplasma genitalium* nucleic acid template, said amplification oligonucleotide comprising a nucleotide sequence selected from the group consisting of:

| SEQ ID NO: 84 | CTGCTGGCAC ATAGTTAGTC GTC, |
| --- | --- |
| SEQ ID NO: 51: | GGATTGAAAA GTCTGGTGTT AAAGGCAGCT GC, |
| SEQ ID NO: 82: | CGCCACTGGT GTTCCTTCAT ATATCTACGC, | and RNA equivalents thereto; and b) amplifying said template.

24. The method of claim 23, wherein said amplification oligonucleotide further comprises a nucleic acid sequence recognized by an RNA polymerase or which enhances initiation or elongation by an RNA polymerase.

* * * * *

UNITED STATES PATENT AND TRADEMARK OFFICE
CERTIFICATE OF CORRECTION

PATENT NO. : 5,656,427
DATED : August 12, 1997
INVENTOR(S) : Hammond et al.

It is certified that error appears in the above-identified patent and that said Letters Patent is hereby corrected as shown below:

Column 51, Line 61, Claim 1: Delete "orals" and insert --orale--

Column 52, Line 61, Claim 1: Delete "pneumonias" and insert --pneumoniae--

Column 53, Line 15, Claim 1: Delete "pneumonias" and insert --pneumoniae--

Column 53, Line 27, Claim 2, SEQ ID NO:2:
    Delete "CACACTATAG" and insert-- CACACTCTAG--

Column 53, Line 48, Claim 5, in SEQ ID NO:7:
    Delete " CCTTTTGCG" and insert-- CCTTTTGCGC--

Column 54, Line 38, Claim 12: Delete "pneumonias" and insert --pneumoniae--

Column 56, Line 34, Claim 22, in SEQ ID NO:83:
    Delete "CAASGGGTTCG" and insert--CAAGGGTTCG--

Column 56, Line 54, Claim 23, Delete "pneumonias" and insert --pneumoniae--

Signed and Sealed this

Twenty-fifth Day of May, 1999

Attest:

Q. TODD DICKINSON

Attesting Officer      Acting Commissioner of Patents and Trademarks